United States Patent
Cherry et al.

[11] Patent Number: 5,990,156
[45] Date of Patent: Nov. 23, 1999

[54] 6-CARBOXAMIDO DIHYDROPYRAN DERIVATIVES

[75] Inventors: Peter Cherry; Peter Howes; Paul Smith; Stephen Sollis, all of Hertfordshire, United Kingdom

[73] Assignee: Biota Scientific Management PTY Ltd., Melbourne, Australia

[21] Appl. No.: 08/945,676

[22] PCT Filed: May 13, 1996

[86] PCT No.: PCT/AU96/00289

§ 371 Date: Jan. 12, 1998

§ 102(e) Date: Jan. 12, 1998

[87] PCT Pub. No.: WO96/36628

PCT Pub. Date: Nov. 21, 1996

[30] Foreign Application Priority Data

May 19, 1995 [GB] United Kingdom ........... 9510141.6
Dec. 12, 1995 [GB] United Kingdom ........... 9525389.4

[51] Int. Cl.⁶ .......................... A61K 31/35; C07D 315/00
[52] U.S. Cl. .......................... 514/459; 514/460; 549/420; 549/424
[58] Field of Search .................. 549/420, 424; 514/459, 460

[56] References Cited

FOREIGN PATENT DOCUMENTS

27579/71 10/1992 Australia.
24566/92 3/1993 Australia.
27242/92 4/1993 Australia.
91/16320 10/1991 WIPO.
93/16049 8/1993 WIPO.

OTHER PUBLICATIONS

Sollis, et al., "Novel Inhibitors of Influenza Sialidase Related to GG167 Synthesis of 4–Amino abd Guanidino–4H Pyran–2–Carboxylic Acid–6–Propylamides; Selective Inhibitors of Influenza A Virus Sialidase", Bioorganic & Medicinal Chemistry Letters, pp. 8–11.

Primary Examiner—Amelia Owens
Attorney, Agent, or Firm—Foley & Lardner

[57] ABSTRACT

Compounds of formula (I),

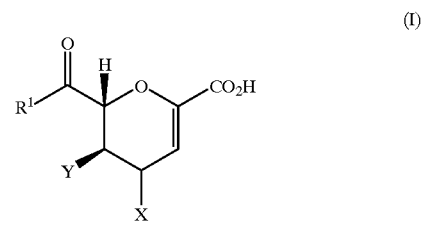

wherein $R^1$ represents $OR^5$, $SR^5$, $NR^5R^6$, $N(OR^5)R^6$ or $N(NR^5R^6)R^6$; X represents OH, $N_3$, $NR^3R^4$ or $NR^4CO_2R^{15}$; Y represents H or $NHR^2$; $R^2$ represents a group $SO_2R^7$ or $COR^7$; $R^3$ represents H, $C_{1-6}$alkyl or $C(=NR^8)NR^9R^{10}$; $R^4$ represents H or $C_{1-6}$alkyl; $R^5$ represents H, $C_{1-20}$alkyl, $C_{3-8}$cycloalkyl, $C_{2-20}$alkenyl, $C_{2-20}$alkynyl, $CHR^{11}COR^{12}$ or $C_{1-20}$alkyl substituted by one or more groups selected from $NR^{13}R^{14}$, $NR^{13}COR^{14}$, $CO_2R^{13}$, $OR^{13}$, $C_{3-8}$cycloalkyl and optionally substituted aryl; each $R^6$ independently represents H, $C_{1-6}$alkyl, $C_{3-8}$cycloalkyl, $C_{2-6}$alkenyl, $C_{2-20}$alkynyl, aryl or $C_{1-4}$alkyl substituted by one or more groups selected from $NR^{13}R^{14}$, $COR^{13}$, $C_{3-8}$cycloalkyl, CN, $N_3$, $OR^{13}$ and optionally substituted aryl; or $R^5$ and $R^6$ together form a $C_{2-6}$ hydrocarbon chain which may optionally contain a group $NR^{13}$ which chain is optionally substituted by 1, 2, 3 or 4 groups selected from oxo and $C_{1-6}$alkyl groups which groups may optionally be substituted by hydroxy or optionally substituted aryl; $R^7$ represents $C_{1-6}$alkyl optionally substituted by one or more halogen atoms, $C_{3-8}$cycloalkyl or optionally substituted aryl; $R^8$, $R^9$ and $R^{10}$ each independently represent H, $C_{1-6}$alkyl, amino, hydroxy, cyano or nitro; $R^{11}$ represents the side chain of a D- or L-amino acid; $R^{12}$ represents $NR^{13}R^{14}$, $OR^{13}$ or $R^{13}$; each $R^{13}$ and each $R^{14}$ independently represents H, $C_{1-6}$alkyl or optionally substituted aryl$C_{1-4}$alkyl; $R^{15}$ represents $C_{1-6}$alkyl; and their pharmaceutically acceptable derivatives are neuraminidase inhibitors useful in the treatment of viral infections.

11 Claims, No Drawings

6-CARBOXAMIDO DIHYDROPYRAN DERIVATIVES

This invention relates to a new class of chemical compounds and to their use in medicine. In particular the invention concerns novel dihydropyran derivatives, methods for their preparation, pharmaceutical formulations thereof and their use as antiviral agents.

Enzymes with the ability to cleave N-acetyl neuraminic acid (NANA), also known as sialic acid, from other sugars are present in many microorganisms. These include bacteria such as Vibrio cholerae, Clostridium perfringens, Streptococcus pneumoniae, and Arthrobacter sialophilus, and viruses such as influenza virus, parainfluenza virus, mumps virus, Newcastle disease virus, and Sendai virus. Most of these viruses are of the orthomyxovirus or paramyxovirus groups, and carry a neuraminidase activity on the surface of the virus particles.

Many of the neuraminidase-possessing organisms are major pathogens of man and/or animals, and some, such as influenza virus and Newcastle disease virus, cause diseases of enormous economic importance.

It has long been thought that inhibitors of neuraminidase activity might prevent infection by neuraminidase-bearing viruses. Most of the known neuraminidase inhibitors are analogues of neuraminic acid, such as 2-deoxy-2,3-didehydro-N-acetylneuraminic acid (DANA) and its derivatives. See, e.g., Meindl et al., Virology 1974 58 457–63. International Application Publication No. WO91/16320 describes a number of derivatives of DANA active both in vitro and in vivo against viral neuraminidase and useful in the treatment of influenza. Further DANA derivatives are disclosed in EP 0539204, WO 95/18800 and WO 95/20583. None of these publications discloses compounds having a carboxamide group at the 6 position of the dihydropyran ring.

We have now found a novel class of dihydropyran derivatives which are active against the influenza virus.

The invention therefore provides, in a first aspect, compounds of formula (I)

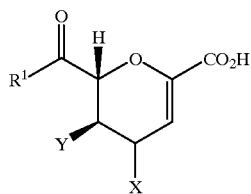

(I)

wherein
$R^1$ represents $OR^5$, $SR^5$, $NR^5R^6$, $N(OR^5)R^6$ or $N(NR^5R^6)R^6$;
X represents OH, $N_3$, $NR^3R^4$ or $NR^4CO_2R^{15}$;
Y represents H or $NHR^2$;
$R^2$ represents a group $SO_2R^7$ or $COR^7$;
$R^3$ represents H, $C_{1-6}$alkyl or $C(=NR^8)NR^9R^{10}$;
$R^4$ represents H or $C_{1-6}$alkyl;
$R^5$ represents H, $C_{1-20}$alkyl, $C_{3-8}$cycloalkyl, $C_{2-20}$alkenyl, $C_{2-20}$alkynyl, $CHR^{11}COR^{12}$ or $C_{1-20}$alkyl substituted by one or more groups selected from $NR^{13}R^{14}$, $NR^{13}COR^{14}$, $CO_2R^{13}$, $OR^{13}$, $C_{3-8}$cycloalkyl and optionally substituted aryl;
Each $R^6$ independently represents H, $C_{1-6}$alkyl, $C_{3-8}$cycloalkyl, $C_{2-6}$alkenyl, $C_{2-20}$ alkynyl, aryl, or $C_{1-4}$alkyl substituted by one or more groups selected from $NR^{13}R^{14}$, $COR^{13}$, $C_{3-8}$cycloalkyl, CN, $N_3$, $OR^{13}$ and optionally substituted aryl;

or $R^5$ and $R^6$ together form a $C_{2-6}$ hydrocarbon chain which may optionally contain a group $NR^{13}$ which chain is optionally substituted by 1, 2, 3, or 4 groups selected from oxo and $C_{1-6}$alkyl groups which groups may optionally be substituted by hydroxy or optionally substituted aryl;
$R^7$ represents $C_{1-6}$alkyl optionally substituted by one or more halogen atoms, $C_{3-8}$cycloalkyl or optionally substituted aryl;
$R^8$, $R^9$ and $R^{10}$ each independently represent H, $C_{1-6}$alkyl, amino, hydroxy, cyano or nitro;
$R^{11}$ represents the side chain of a D- or L-amino acid;
$R^{12}$ represents $NR^{13}R^{14}$, $OR^{13}$ or $R^{13}$;
each $R^{13}$ and each $R^{14}$ independently represents H, $C_{1-6}$alkyl or optionally substituted aryl$C_{1-4}$alkyl;
$R^{15}$ represents $C_{1-6}$alkyl;
and their pharmaceutically acceptable derivatives.

Preferably $R^1$ represents $NR^5R^6$ or $N(OR^5)R^6$, more preferably $NR^5R^6$.
Suitably $R^5$ is selected from substituted or unsubstituted $C_{1-10}$alkyl, $C_{2-6}$alkenyl or $C_{3-8}$cycloalkyl and $R^6$ is substituted or unsubstituted $C_{1-6}$alkyl, H or aryl or $R^5$ and $R^6$ together with the nitrogen atom to which they are joined form a group

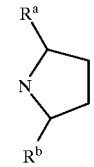

where $R^a$ and $R^b$ independently represent H, $C_{1-6}$alkyl such as methyl or hydroxymethyl, preferably H or methyl.
More preferably $R^1$ represents $NR^5R^6$ and $R^5$ and $R^6$ both represent $C_{1-6}$alkyl groups optionally substituted by optionally substituted aryl or cycloalkyl, or $NR^5R^6$ represents a group

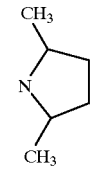

Preferably Y represents $NHR^2$. More preferably Y represents $NHCOR^7$ wherein $R^7$ represents $C_{1-2}$alkyl optionally substituted by one or more fluorine atoms, such as methyl, ethyl or trifluoromethyl, more preferably methyl.
One subgroup of compounds according to the invention is represented by formula (Ia):

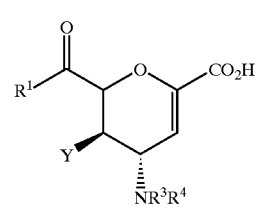

(Ia)

wherein $R^1$ and Y are as defined for formula (I) above. In compounds of formula (Ia), $NR^3R^4$ preferably represents amino or guanidino, more preferably guanidino.

A further subgroup of compounds of the invention is represented by formula (Ib):

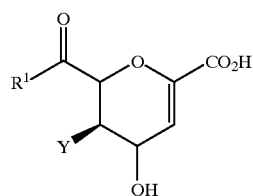

(Ib)

wherein $R^1$ and Y are as defined for formula (I) above.

The D- or L-amino acids of which $R^{11}$ represents the side chain may be natural amino acids, such as glycine, alanin, valine, leucine, isoleucine, serine, threonine, phenylalanine, tyrosine, tryptophan, cysteine, proline, methionine, aspartic acid, asparagine, glutamic acid, glutamine, arginine, lysine or histidine; or unnatural amino acids.

As used herein, alkyl includes both straight and branched chain saturated hydrocarbon groups.

As used herein, alkenyl means a straight or branched hydrocarbon chain containing one or more carbon-carbon double bonds.

As used herein, alkynyl means a straight or branched hydrocarbon chain containing one or more carbon-carbon triple bonds.

Aryl means aromatic carbocyclic and heterocyclic groups. Preferred examples of aryl groups included phenyl, naphthyl, pyridyl, imidazolyl and thienyl. When aryl groups are optionally substituted, suitable substituents include $C_{1-4}$alkyl, $C_{1-4}$alkoxy, halo, hydroxy, cyano, nitro, trifluoromethyl, amino, phenyl and benzyl. Suitably, substituted aryl groups bear 1, 2 or 3 substituents.

By "a pharmaceutically acceptable derivative" is meant any pharmaceutically acceptable salt, ester, or salt of such ester, of a compound of formula (I) or any other compound which, upon administration to the recipient, is capable of providing (directly or indirectly) a compound of formula (I) or an antivirally active metabolite or residue thereof.

It will be appreciated by those skilled in the art that the compounds of formula (I) may be modified to provide pharmaceutically acceptable derivatives thereof at any of the functional groups in the compounds of formula (I). Of particular interest as such derivatives are compounds modified at the carboxyl function, hydroxyl functions or at amino groups. Thus compounds of interest include alkyl (such as methyl, ethyl or propyl e.g. isopropyl) or aryl (e.g. phenyl, benzoyl) esters and acetyl esters of the compounds of formula (I).

It will be appreciated by those skilled in the art that the pharmaceutically acceptable derivatives of the compounds of formula (I) may be derivatised at more than one position.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene- p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable may be useful in the preparation of salts useful as intermediates in obtaining compounds of the invention and their pharmaceutically acceptable acid addition salts.

Salts derived from appropriate bases include alkali metal (e.g. sodium), alkaline earth metal (e.g. magnesium), ammonium and $NR_4^+$ (where R is $C_{1-4}$alkyl) salts.

As preferred subgroup of compounds according to the invention is represented by formula (Ic):

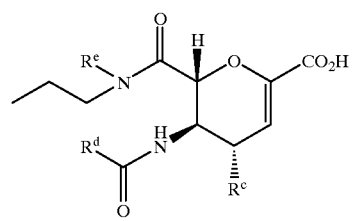

(Ic)

wherein
$R^c$ is $NH_2$ or $NHC(=NH)NH_2$;
$R^d$ is $C_{1-2}$alkyl optionally substituted by one or more fluorine atoms;
$R^e$ is $C_{2-8}$alkyl optionally substituted by phenyl, naphthyl or biphenyl, preferably ethyl substituted by phenyl, naphthyl or biphenyl;
or a pharmaceutically acceptable salts thereof.

Preferred compounds include:
(4S,5R,6R)-5-acetylamino-6-dimethylcarbamoyl-4-guanidino-5,6-dihydro-4H-pyran-2-carboxylic acid;
(4S,5R,6R)-5-acetylamino-6-(methylpropylcarbamoyl)-4-guanidino-5,6-dihydro-4H-pyran-2-carboxylic acid;
(4S,5R,6R)-5-acetylamino-4-amino-6-(2,5-dimethylpyrrolidine-1-carbonyl)-5,6-dihydro-4H-pyran-2-carboxylic acid;
(4S,5R,6R)-5-acetylamino-4-amino-6-dipropylcarbamoyl-5,6-dihydro-4H-pyran-2-carboxylic acid;
(4S,5R,6R)-5-acetylamino-6-dipropylcarbamoyl-4-guanidino-5,6-dihydro-4H-pyran-2-carboxylic acid;
(4S,5R,6R)-5-acetylamino-6-dibutylcarbamoyl-4-guanidino-5,6-dihydro-4H-pyran-2-carboxylic acid;
(4S,5R,6R)-5-acetylamino-4-amino-6-(phenylethylpropylcarbamoyl)-5,6-dihydro-4H-pyran-2-carboxylic acid;
(4S,5R,6R)-5-acetylamino-6-(phenylethylpropylcarbamoyl)-4-guanidino-5,6-dihydro-4H-pyran-2-carboxylic acid;
(4S,5R,6R)-5-acetylamino-4-amino-6-(butylpropylcarbamoyl)-5,6-dihydro-4H-pyran-2-carboxylic acid;
(4S,5R,6R)-5-acetylamino-4-amino-6-diethylcarbamoyl-5,6-dihydro-4H-pyran-2-carboxylic acid;
(4S,5R,6R)-5-acetylamino-4-amino-6-(ethylpropylcarbamoyl)-5,6-dihydro-4H-pyran-2-carboxylic acid;
(4S,5R,6R)-4-Amino-6-(dipropylcarbamoyl)-5-(2,2,2-trifluoroacetylamino)-5,6-dihydro-4H-pyran-2-carboxylic acid;
(4S,5R,6R)-5-Acetylamino-4-amino-6-[(2-naphthalen-2-yl-ethyl) propylcarbamoyl]-5,6-dihydro-4H-pyran-2-carboxylic acid;
(4S,5R,6R)-5-acetylamino-4-amino-6-[(2-biphenyl-4-yl-ethyl)carbamoyl]-5,6-dihydro-4H-pyran-2-carboxylic acid;
(4S,5R,6R)-5-Acetylamino-6-[(2-cyclohexylethyl) propylcarbamoyl]-4-guanidino-5,6-dihydro-4H-pyran-2-carboxylic acid;
(4S,5R,6R)-5-Acetylamino-6-[(4-biphenylethylpropylcarbamoyl]-4-guanidino-5,6-dihydro-4H-pyran-2-carboxylic acid;
(4S,5R,6R)-4-Amino-6-(phenethylpropylcarbamoyl)-5-propionylamino-5,6-dihydro-4H-pyran-2-carboxylic acid;

and pharmaceutically acceptable derivatives thereof.

References hereinafter to a compound of the invention includes the compounds of formula (I) and pharmaceutically acceptable derivatives thereof.

The compounds of formula (I) possess antiviral activity. In particular these compounds are inhibitors of viral neuraminidase of orthomyxoviruses and paramyxoviruses in particular influenza neuraminidase, for example the viral neuraminidase of influenza A and B.

Compounds of the examples have been tested for the ability to inhibit the multiplication of influenza virus in a plaque reduction assay essentially as described WO91/16320. Typically, $IC_{50}$ values for influenza A and B were less than 50 μg/ml.

There is thus provided in a further aspect of the invention a compound of formula (I) or a pharmaceutically acceptable derivative thereof for use as an active therapeutic agent in particular as an antiviral agent for example in the treatment of influenza virus infections.

In a further or alternative aspect there is provided a method for the treatment of a viral infection, for example an influenza virus infection in a mammal including man comprising administration of an effective amount of a compound of formula (I) or a pharmaceutically acceptable salt or derivative thereof.

There is also provided in a further or alternative aspect use of a compound of the invention for the manufacture of a medicament for the treatment of a viral infection.

It will be appreciated by those skilled in the art that reference herein to treatment extends to prophylaxis as well as the treatment of established infections or symptoms.

The compounds of the invention may also be used in disagnostic methods, in particular methods for the detection of influenza virus. For use in such methods it may be advantageous to link a compound of the invention to a detachable label.

In a further or alternative aspect, the present invention provides a compound of formula (I) for use in medicine. As used herein the term "medicine" includes both treatment and diagnosis.

The amount of a compound of the invention required for use in treatment will vary not only with the particular compound selected but also with the route of administration, the nature of the condition being treated and the age and condition of the patient and will ultimately be at the discretion of the attendant physician or veterinarian. In general however a suitable dose will be in the range of from about 0.1 to 750 mg/kg of bodyweight per day, preferably in the range of 0.5 to 60 mg/kg/day, most preferably in the range of 1 to 20 mg/kg/day.

Treatment is preferably commenced before or at the time of infection and continued until virus is no longer present in the respiratory tract. However the compounds are also effective when given post-infection, for example after the appearance of established symptoms.

Suitably treatment is given 1–4 times daily and continued for 3–7, e.g. 5 days post infection depending upon the particular compound used.

The desired dose may be presented in a single dose or as divided doses administered at appropriate intervals, for example as two, three, four or more sub-doses per day.

The compound is conveniently administered in unit dosage form for example containing 10 to 1500 mg, conveniently 20 to 1000 mg, most conveniently 50 to 700 mg of active ingredient per unit dosage form.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt or derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration to the respiratory tract (including the nasal passages) for example by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tables each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth;

pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

Preferably the compound of the invention will be administered to the respiratory tract.

For administration to the respiratory tract (including intranasal administration) the neuraminidase inhibitors may be administered by any of the methods and formulations employed in the art for administration to the respiratory tract, including inhalation via the nose and/or mouth using a nebuliser or an inhaler.

Thus in general the compounds may be administered in the form of a solution or a suspension or as a dry powder.

Solutions and suspensions will generally be aqueous for example prepared from water alone (for example sterile or pyrogen-free water) or water and a physiologically acceptable co-solvent (for example ethanol, propylene glycol, polyethylene glycols such as PEG 400).

Such solutions or suspensions may additionally contain other excipients for example preservative (such as benzalkonium chloride), solubilising agents/surfactants such as polysorbates (e.g. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant such as a chlorofluorocarbon (CFC) for example dichlorodifluoromethane, trichlorofluoromethane or dichlorotetrafluroroethane, carbon dioxide or other suitable gas. The aerosol may conveniently also contain a surfactant such as lecithin. The dose of drug may be controlled by provision of a metered valve.

Alternatively the compounds may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronisation.

When desired, formulations adapted to give sustained release of the active ingredient may be employed.

The compounds of the invention may also be used in combination with other therapeutic agents, for example other anti-infective agents. In particular the compounds of the invention may be employed with other antiviral agents. The invention thus provides in a further aspect a combination comprising a compound of formula (I) or a pharmaceutically acceptable salt or derivative thereof together with another therapeutically active agent, in particular an antiviral agent.

The combinations referred to above may conveniently be presented for use in the form of a pharmaceutical formulation and thus such formulations comprising a combination as defined above together with a pharmaceutically acceptable carrier therefor comprise a further aspect of the invention.

Suitable therapeutic agents for use in such combinations include other anti-infective agents, in particular antibacterial and anti-viral agents such as those used to treat respiratory infections. For example, other compounds effective against influenza viruses, such as amantadine, rimantadine and ribavirin, may be included in such combinations.

The individual components of such combinations may be administered either sequentially or simultaneously in separate or combined pharmaceutical formulations.

When the compounds of the invention are used with a second therapeutic agent active against the same virus the dose of each compound may either be the same as or differ from that employed when each compound is used alone. Appropriate doses will be readily appreciated by those skilled in the art.

The compounds of formula (I) and their pharmaceutically acceptable salts and derivatives may be prepared by the methods described below in which R, $R^1$, $R^2$, $R^3$ $R^4$, $R^5$ and R are as defined for formulate (I) unless otherwise specified. The methods outlined below form a further aspect of the invention.

In one such process (A) compounds of formula (I) wherein $R^1$ is hydroxy may be prepared from compounds of formula (II)

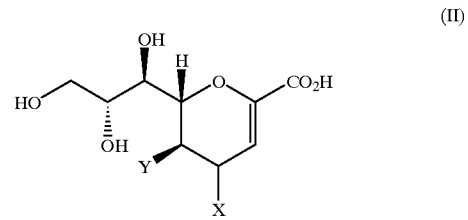

or a suitably protected derivative thereof, by oxidative cleavage of the glycerol sidechain, followed, if necessary, by deprotection.

Conveniently the oxidative cleavage is carried out in two steps. Suitably the first step is effected using a periodate, such as, for example, sodium periodate, conveniently in a suitable solvent, such as an aqueous organic solvent, for example, aqueous methanol. Suitable reagents for the second step of the oxidative cleavage include chlorites, for example sodium chlorite, suitably in the presence of a buffering agent, such as an alkali or alkline earth metal phosphate for example, potassium phosphate, in an aqueous organic solvent, such as an aqueous mixture of an alcohol and a hydrocarbon, for example, an aqueous mixture of t-butanol and cyclohexene.

Compounds of formula (I) wherein $R^1$ is $OR^5$ and $R^5$ is other than H may be prepared from the corresponding compounds wherein $R^5$ is H by conventional alkylation procedures.

Compounds of formula (I) wherein $R^1$ is other than $OR^5$ may be prepared from the corresponding compounds of formula (I) wherein $R^1$ represents hydroxy by reaction with a suitably substituted amine. Suitably the hydroxy group is activated prior to reaction with the amine. Suitable methods of activation will be readily apparent to those skilled in the art and include, for example, conversion to a pentafluorophenoxy group. The amination is conveniently effected in a suitable organic solvent such as an ether, for example, tetrahydrofuran.

Other compounds of formula (I) may be prepared by interconversion of different compounds of formula (I). For example, compounds wherein $R^3$ and $R^4$ are other than H may be prepared by derivatisation of the corresponding compound wherein $R^3$ and/or $R^4$ are H.

According to an alternative process (B), compounds of formula (I) wherein X is $NH_2$ may be prepared from the corresponding compounds of formula (III):

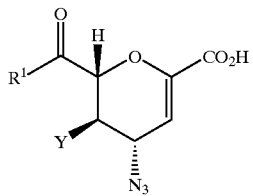

(III)

or protected derivatives thereof, by reduction of the azide group, followed, if necessary, by deprotection.

The reduction may be carried out using any known methods for the conversion of azides to amines. Suitable methods are described in the Examples hereinafter and, for example, in International patent application publication numbers WO93/12105 and WO95/00503. Conveniently, the reduction is achieved using triphenylphosphine.

Compounds of formula (I) wherein X is substituted amine or guanidine may be prepared from compounds of formula (I) wherein X is $NH_2$ by suitable derivatisation of the amine. In particular, compounds of formula (I) wherein X represents guanidine may be prepared from the corresponding compounds of formula (I) wherein X is $NH_2$, for example by reaction with pyrazolcarboxamidine, or a salt or derivative thereof, preferably pyrazolcarboxamidine hydrochloride.

As will be appreciated by those skilled in the art it may be necessary or desirable at any stage in the above described processes to protect one or more sensitive groups in the molecule to prevent undesirable side reactions; the protecting group may be removed at any convenient subsequent stage in the reaction sequence.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene and P G M Wuts (John Wiley and Sons 1991).

Conventional amino protecting groups may include for example aralkyl groups, such as benzyl, diphenylmethyl or triphenylemthyl groups; and acyl groups such as N-benzyloxycarbonyl or t-butoxycarbonyl.

Hydroxy groups may be protected, for example, by aralkyl groups, such as benzyl, diphenylmethyl or triphenylmethyl groups, acyl groups, such as acetyl, silicon protecting groups, such as trimethylsilyl groups, or as tetrahydropyran derivatives.

Carboxylic acid groups are conveniently protected as the methyl or diphenylmethyl esters.

Removal of any protecting groups present may be achieved by conventional procedures.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

The present invention is further described by the following examples which are for illustrative purposes only and should not be construed as a limitation of the invention.

EXAMPLE 1

(4S,5R,6R)-5-Acetylamino-4-amino-6-(methylpropylcarbamoyl)-5,6-dihydro-4H-pyran-2-carboxylic acid trifluoroacetate salt a) (4S,5R,6R)-5-Acetylamino-4-(tert-butoxycarbonylamino)-6-(1R,2R,3-trihydroxy-propyl)-5,6-dihydro-4H-pyran-2-carboxylic acid benzhydryl ester To a suspension of (4S,5R,6R)-5-acetylamino-4-amino-6-(1R,2R,3-trihydroxy-propyl)-5,6-dihydro-4H-pyran-2-carboxylic acid trihydrate (8.25 g,) in dioxan/water (2:1 v/v, 75 ml) was added sodium bicarbonate (2.6 g) and di-t-butyl pyrocarbonate (6.76 g) and the reaction was stirred at 23° C. for 18 hours. The resulting solution was acidified to pH6 using 2N hydrochloric acid and to this was added a solution of diphenyldiazomethane in dichloromethane (125 ml of a 0.29M solution). This was stirred rapidly for 24 hours whilst maintaining the pH at approximately 6 using 2N hydrochloric acid. The resulting suspension was filtered and the solid was dried in vacuo to give the title compound. (10.9 g); $^1$H NMR (250 MHz, $D_6$-DMSO) 8.13 (1H, d, J=8Hz), 7.49–7.25 (10H, m), 7.15 (1H, d, J=8.75Hz), 6.87 (1H, s), 5.88 (1H, m), 4.63 (2H, m), 4.47 (1H, m), 4.34 (1H, m), 4.18 (1H, m), 3.91 (1H, m), 3.67 (2H, m), 3.40 (2H, m), 1.88 (3H, s), 1.41 (9H, s); Mass spec (Low resolution): $MH^+$=557, $MH^+$-BOC=457; Mass analysis: $C_{29}H_{36}N_2O_9 \cdot 1.5H_2O$. Required: C,59.68; H, 6.74; N, 4.80. Found: C, 59.65; H, 6.61; N, 4.84.

b) (2R,3R,4S)-3-Acetylamino-4-(tert-butoxycarbonylamino)-3,4-dihydro-2H-pyran-2,6-dicarboxylic acid 6-benzhydryl ester (4S,5R,6R)-5-Acetylamino-4-(tert-butoxycarbonylamino)-6-(1R,2R,3-trihydroxy-propyl)-5,6-dihydro-4H-pyran-2-carboxylic acid benzhydryl ester (8.0 g) was dissolved in methanol/water (5:1 v/v, 180 ml). To this was added sodium periodate (6.93 g) and the reaction was stirred at 23° C. for 3 hours. The solid was removed by filtration and the filtrate was evaporated in vacuo to give a white solid.

The solid obtained by evaporation of the filtrate was suspended in t-butanol (70 ml) and cyclohexene (10 ml) and stirred rapidly at 23° C. To this was added a solution of sodium chlorite (10.7 g) and potassium dihydrogen orthophosphate (10.7 g) in water (50 ml). After 18 hours a pale yellow solution was obtained which was acidified using 2N hydrochloric acid. This was extracted into ethyl acetate (3×200 ml) and dried over anhydrous magnesium sulphate. The solvent was removed in vacuo and the residue was triturated with diethyl ether. The solid was collected by filtration and dried to give the title compound. (5.1 g). $^1$H NMR (250 MHz, D$_6$-DMSO). 13.1 (1H, broad s), 7.96 (1H, d, J=8.75Hz), 7.48–7.26 (10H, m), 6.92 (1H, s), 6.83 (1H, d, J=6.25Hz), 6.06 (1H, d, J=3Hz), 4.57 (1H, d, J=6.25Hz), 4.28 (1H, m), 4.15 (1H, m), 1.79 (3H, s), 1.38 (9H, s): Mass analysis:

C$_{27}$H$_{30}$N$_2$O$_8$. 0.25H$_2$O.Required: C, 62.96; H, 5.97; N, 5.44.Found: C, 62.85; H, 5.93; N, 5.52; Mass Spec (Low resolution): MH$^+$=511 c) (2R,3R,4S)-3-Acetylamino-4-(tert-butoxycarbonylamino)-3,4-dihydro-2H-pyran-2,6-dicarboxylic acid 6-benzhydryl ester 2-(2,3,4,5,6-pentafluoro-phenyl) ester (2R,3R,4S)-3-Acetylamino-4-(tert-butoxycarbonylamino)-3,4-dihydro-2H-pyran-2,6-dicarboxylic acid 6-benzhydryl ester (3.36 g) was dissolved in dry dimethylformamide (10 ml) and pyridine (0.632 g) under nitrogen and stirred at 23° C. To this was added pentafluorophenyl trifluoroacetate (2.02 g). After 3 hours the reaction mixture was diluted with ethyl acetate (250 ml) and washed with dilute hydrochloric acid (3×50 ml), dilute sodium bicarbonate solution (3×50 ml) and brine (50 ml). The organic phase was dried over anhydrous magnesium sulphate and the solvent was removed in vacuo to give the title compound as an off-white foam. (4.353 g); $^1$H NMR (250 MHz, DMSO) 8.22 (1H, d, J=8Hz), 7.50–7.27 (10H, m), 7.06 (1H, m), 6.94 (1H, s), 6.18 (1H, d, J=3.8Hz), 5.25 (1H, d, J=6.8Hz), 4.42 (1H, m), 4.29 (1H, m), 1.82 (3H, s), 1.38 (9H, s).

d) (4S,5R,6R)-5-Acetylamino-4-(tert-butoxycarbonylamino)-6-(methylpropylcarbamoyl)-5,6-dihydro-4H-pyran-2-carboxylic acid benzhydryl ester To (2R,3R,4S)-3-acetylamino-4-(tert-butoxycarbonylamino)-3,4-dihydro-2H-pyran-2,6-dicarboxylic acid 6-benzhydryl ester 2-(2,3,4,5,6-pentafluoro-phenyl) ester (1.18 g) in dry tetrahydroduran (13 ml) was added N-methyl-propylamine (0.152 g) and the reaction was stirred at 23° C. for 4 hours. The solvent was removed in vacuo and the residue was chromatographed over silica (Merck 9385, 150 g) using medium pressure (~4 psi) and ethyl acetate as the eluant. The required fractions were combined and the solvent removed in vacuo to give the title compound as a white foam. (0.85 g); $^1$H NMR (250 MHz, D$_6$-DMSO) 8.10–7.98 (1H, m), 7.48–7.26 (10H, m), 6.91 (1H, s), 6.58 (1H, m), 6.03 (1H, m), 5.13 (1H, m), 4.34 (1H, m), 4.03 (1H, m), 3.37 (2H, m), 3.07+2.81 (3H, s), 1.77 (3H, s), 1.64–1.22 (2H, m), 1.37 (9H, s), 0.81 (3H, m): Mass spec (Low resolution): MH$^+$=566, MH$^+$–BOC=466; Mass analysis:

C$_{31}$H$_{39}$N$_3$O$_7$.0.5C$_6$HF$_5$O. Required: C, 62.09; H, 6.05; N, 6.39. Found: C, 61.85; H, 6.07; N, 6.43.

e) (4S,5R,6R)-5-Acetylamino-4-amino-6-(methylpropylcarbamoyl)-5,6-dihydro-4H-pyran-2-carboxylic acid trifluoroacetate salt (4S,5R,6R)-5-Acetylamino-4-(tert-butoxycarbonylamino)-6-(methyl-propylcarbamoyl)-5,6-dihydro-4H-pyran-2-carboxylic acid benzhydryl ester (0.10 g) was dissolved in dichloromethane (1 ml) and trifluoro-acetic acid (1 ml) and left to stand at 23° C. for 3 hours. The solvent was removed in vacuo and the residue was triturated using diethyl ether (30 ml). The resulting solid was collected by filtration and dried to give the title compound as a white solid. (0.064 g): $^1$H NMR (250MHz, D$_2$O) 5.99 (1H, m), 5.24 (1H, m), 4.52 (1H, m), 4.25 (1H, m), 3.59–3.18 (2H, m), 3.18+2.97 (3H, s), 2.02 (3H, s), 1.72–1.46 (2H, m), 0.87 (3H, m); Mass Analysis: C$_{15}$H$_{22}$F$_3$N$_3$O$_7$. 0.25H$_2$O. Required C, 43.12; H, 5.43; N, 10.06; Found C, 42.99; H, 5.60; N, 10.17; Mass Spec. (Low Resolution) MH$^+$=300.

EXAMPLE 2

(4S,5R,6R)-5-Acetylamino-6-(methylpropylcarbamoyl)-4-guanidino-5,6-dihydro-4H-pyran-2-carboxylic acid trifluoroacetate salt a) (4S,5R,6R)-5-Acetylamino-4-[2,3-bis(tert-butoxycarbonyl)-guanidino]-6-(methylpropylcarbamoyl)-5,6-dihydro-4H-pyran-2-carboxylic acid benzhydryl ester (4S,5R,6R)-5-Acetylamino-4-(tert-butoxycarbonylamino)-6-(methylpropylcarbamoyl)-5,6-dihydro-4H-pyran-2-carboxylic acid benzhydryl ester (0.83 g) was dissolved in a solution of hydrogen chloride in dioxane (10 ml of a 4.0N solution) and stirred under nitrogen for 30 minutes. The solvent was removed in vacuo to give an off-white foam. This was suspended in tetrahydrofuran (10 ml) and dimethylformamide (5 ml). To this was added triethylamine (0.42 ml) and (tert-butoxycarbonylimino)-pyrazol-1-yl-methylcarbamic acid tert-butyl ester (0.682 g) and the reaction was stirred at 23° C. for 18 hours. The reaction was partitioned between ethyl acetate and 1N hydrochloric acid. The organic phase was dried over anhydrous magnesium sulphate and the solvent was removed in vacuo. The residue was chromatographed over silica (Merck 9385, 30 g) using medium pressure (~4 psi) and cyclohexane/ethyl acetate (1:1 v/v) as eluant. The required fractions were combined and the solvent was removed in vacuo to give the title compound as a white foam. (0.607 g); $^1$H NMR (250 MHz, D$_6$-DMSO) 11.41 (1H, s), 8.63 (1H, m), 7.40–7.29 (10H, m), 6.99 (1H, s), 6.12 (1H, m), 5.85 (1H, m), 5.16 (1H, m), 5.04 (1H, m), 4.33 (1H, m), 3.45 (2H, m), 3.17+2.89 (3H, s), 1.98 (3H, s), 1.69–1.42 (2H, m), 1.49 (18H, s), 0.87 (3H, m); Mass Spec (Low resolution):MH$^+$= 708, MH$^+$–BOC=608, MH$^+$–2BOC=508;

Mass analysis: C$_{37}$H$_{49}$N$_5$O$_9$. 0.75H$_2$O. Required: C, 61.61; H, 7.06; N, 9.71. Found: C, 61.81; H, 6.85; N, 9.73.

b) (4S,5R,6R)-5-Acetylamino-6-(methylpropylcarbamoyl)-4-guanidino-5,6-dihydro-4H-pyran-2-carboxylic acid trifluoroacetate salt (4S,5R,6R)-5-Acetylamino-4-[2,3-bis(tert-butoxycarbonyl)-guanidino]-6-(methylpropylcarbamoyl)-5, 6-dihydro-4H-pyran-2-carboxylic acid benzhydryl ester (0.11 g) was dissolved in dichloromethane (1 ml) and trifluoroacetic acid (1 ml) and left to stand for 3 hours. The solvent was removed in vacuo and the residue was triturated using diethyl ether. The solid was collected by filtration and dried to give the title compound as a white solid. (0.061 g) $^1$H NMR (250 MHz, D$_2$O) 6.00 (1H, d, J=4Hz), 5.34 (1H, d, J=6.3Hz), 4.43–4.29 (2H, m) 3.56–3.13 (2H, m), 3.13, 2.93 (3H, 2xs), 2.00 (3H, s), 1.79–1.44 (2H, m), 0.88 (3H, m); Mass analysis:C$_{16}$H$_{24}$F$_3$N$_5$O$_7$. Required C, 42.20; H, 5.31; N15.38. Found C, 42.24; H, 5.45; N, 15.09; Mass Spec (Low resolution):MH$^+$=342.

The following Examples 3–39 were similarly prepared by the methods described in Examples 1 and 2:

EXAMPLE 3

(4S,5R,6R)-5-acetylamino-4-amino-6-propylcarbamoyl-5,6-dihydro-4H-pyran-2-carboxylic acid trifluoroacetate salt $^1$H NMR (250 MHz, D$_2$O) 6.00 (1H, d, J=2.5Hz), 4.54 (1H, d, J=10Hz), 4.42 (1H, t, J=9.4Hz), 4.27 (1H, dd, J=2.5, 9.4Hz), 3.18 (2H, t, J=7Hz), 2.03 (3H, s), 1.51 (2H, sextet, J=7Hz), 0.88 (3H, t, J=7Hz).

EXAMPLE 4

(4S,5R,6R)-5-Acetylamino-6-propylcarbamoyl-4-guanidino-5,6-dihydro-4H-pyran-2-carboxylic acid trifluoroacetate salt $^1$H NMR (250MHz, D$_2$O) 5.88 (1H, d, J=4.5Hz), 4.83 (1H, d), 4.51 (1H, t, J=4.4Hz), 4.28 (1H, t, J=4.4Hz), 3.17 (2H, m), 2.02 (3H, s), 1.49 (2H, m, J=7Hz), 0.88 (3H, t, J=7Hz).

Mass spec (Low resolution): MH$^+$=328. Mass analysis C$_{15}$H$_{22}$F$_3$N$_5$O$_7$. 0.15C$_4$H$_{10}$O. Required: C, 41.16; H, 5.27; N, 15.39. Found: C, 41.24; H, 5.41; N, 15.12.

EXAMPLE 5

(4S,5R,6R)-5-Acetylamino-4-amino-6-dipropylcarbamoyl-5,6-dihydro-4H-pyran-2-carboxylic acid trifluoroacetate salt $^1$H NMR (250MHz, D$_6$—DMSO) 8.20 (1H, d), 6.01 (1H, d), 5.14 (1H, d), 4.37 (1H, q), 4.22 (1H, m), 3.55 (2H, m), 3.32 (1H, m), 3.15 (1H, m), 1.80 (3H, s), 1.65–1.40 (4H, m), 0.85 (6H, m). Mass spec (Low resolution): MH$^+$=328 Mass analysis: C$_{17}$H$_{25}$F$_3$N$_3$O$_7$. H$_2$O. Required: C, 44.44; H, 6.14; N, 9.15. Found: C, 44.72; H, 6.22; N, 9.35.

EXAMPLE 6

(4S,5R,6R)-5-Acetylamino-4-amino-6-dibutylcarbamoyl-5,6-dihydro-4H-pyran-2-carboxylic acid trifluoroacetate salt $^1$H NMR (250MHz, D$_2$O) 5.95 (1H, broad d), 5.16 (1H, d, J=10Hz), 4.48 (1H, t, J=8.5Hz), 4.27 (1H, dd, J=1, 8.5Hz), 3.70–3.10 (4H, m), 2.01 (3H, s), 1.70–1.20 (8H, m), 0.90 (6H, t, J=7.5Hz). Mass spec (Low resolution): MH$^+$=356 Mass Analysis: C$_{19}$H$_{30}$F$_3$N$_3$O$_7$. Required: C, 49.30; H, 6.58; N, 9.17. Found: C, 48.61; H, 6.44; N, 8.95.

EXAMPLE 7

(4S,5R,6R)-5-Acetylamino-4-amino-6-(decylmethylcarbamoyl)-5,6-dihydo-4H-pyran-2-carboxylic acid trifluoroacetate salt $^1$H NMR (250MHz, D$_6$-DMSO, rotamers) 8.1 (1H, two d), 5.8(1H, d), 5.0(1H, two d), 4.1–3.3 (4H, m), 3.0+2.8 (3H, two s), 1.8 (3H, s), 1.6–1.1 (16H,m), 0.9 (3H, t). Mass spec (Low resolution): MH$^+$=398 Mass analysis C$_{22}$H$_{36}$F$_3$N$_3$O$_7$. Required: C, 51.7; H, 7.0; N, 8.2. Found: C, 52,36; H, 7.27; N, 8.68.

EXAMPLE 8

(4S,5R,6R)-5-Acetylamino-4-amino-6-(phenethylpropylcarbamoyl)-5,6-dihydro-4-pyran-2-carboxylic acid trifluoroacetate salt $^1$H NMR (250MHz, D$_2$O) 7.4–7.2 (5H, m), 5.96+5.80 (1H, 2×d), 5.17 (1H, d, J=7.5Hz), 4.6–2.8 (15H, m), 2.01+1.99 (3H, 2×s), 1.7–1.5 (2H, m), 0.86 (3H, t, J=7.5Hz). Mass spec (Low resolution): MH$^+$=390 Mass analysis C$_{22}$H$_{28}$f$_3$N$_3$O$_7$. Required: C, 52.68; H, 5.61; N, 8.35. Found: C, 53.05; H, 5.74; N, 8.41.

EXAMPLE 9

(4S,5R,6R)-5-Acetylamino-4-amino-6-(methoxymethylcarbamoyl)-5,6-dihydro-4H-pyran-2-carboxylic acid trifluoroacetate salt $^1$NMR (250MHz, D$_2$O, rotamers) 6.00 (1H, d, J=2.5Hz), 5.23+5.07 (1H, d, J=10Hz), 4.48 (1H, t, J=10Hz), 4.28 (1H, dd, J=2.5, 10Hz), 3.80+3.71 (3H, two s), 3.48+3.26 (3H, two s), 2.04+2.02 (3H, two s). Mass spec (Low resolution): MH$^+$=288 Mass analysis C$_{13}$H$_{18}$F$_3$N$_3$O$_8$. 0.75H$_2$O. Required: C, 37.64; H, 4.74; N, 10.13. Found: C, 37.65; H, 4.75; N, 9.95.

EXAMPLE 10

(4S,5R,6R)-5-Acetylamino-4-amino-6-(2,5-dimethylpyrrolidinylcarbamoyl)-5,6-dihydro-4H-pyran-2-carboxylic acid trifluoroacetate salt $^1$H NMR (250 MHz, D$_2$O, rotamers) 5.95 (1H, d), 5.10+4.98 (1H, d), 4.58+4.48 (1H, t), 4.4–4.2 (2H, m), 4.0 (1H, m), 2.2–1.9 (3H, s+2H, m), 1.9–1.7 (2H, m), 1.35—1.22 (6H, m). Mass spec (Low resolution): MH$^+$=326 Mass analysis C$_{17}$H$_{24}$F$_3$N$_3$O$_7$. Required: C,47.47; H, 5.51; N, 9.56. Found: C, 46.91; H, 5.77; N, 9.61.

EXAMPLE 11

(4S,5R,6R)-5-Acetylamino-6-dimethylcarbamoyl-4-quanidino-5,6-dihydro-4H-pyran-2-carboxylic acid trifluoroacetate salt $^1$H NMR (250MHz, D$_2$O) 6.01 (1H, d, J=3Hz), 5.34 (1H, d, J=6Hz), 4.38 (2H, m), 3.15 (3H, s), 2.95(3H, s), 2.01 (3H, s). Mass spec (Low resolution):MH$^+$=314 Mass analysis C$_{14}$H$_{20}$F$_3$N$_5$O$_7$.0.1H$_2$O. Required: C, 39.62; H, 4.89; N, 16.04. Found: C, 39.57; H, 4.85; N, 15.81.

EXAMPLE 12

(4S,5R,6R)-5-Acetylamino-4-amino-6-(butylpropylcarbamoyl)-5,6-dihydro-4H-pyran-2-carboxylic acid trifluoroacetate salt $^1$H NMR (D$_6$—DMSO,250MHz) 0.85(6H,m), 1.25(2H,m), 1.35–1.70(4H,m), 1.81(3H,s), 2.95–3.60(4H,m),4.04(1H,d of d), 4.18(1H,q),4.98(1H,d of d), 5.81(1H,s), 8.18(1H,d,J=7.5Hz) Mass spec (Low resolution)MH$^+$=342 Mass analysis C$_{18}$H$_{28}$F$_3$N$_3$O$_7$.Required: C, 47.47; H, 6.20; N, 9.23. Found: C, 47.63; H, 6.23; N, 9.15.

EXAMPLE 13

(4S,5R,6R)-Acetylamino-4-amino-6-diethylcarbamoyl-5,6-dihydro-4H-pyran-2-carboxylic acid trifluoroacetate salt $^1$H NMR (D$_6$—DMSO,250MHz) 1.00(3H,t,J=7.5Hz), 1.15 (3H,t,J=7.5Hz), 1.80(3H,s), 3.10–3.60(4H,m), 4.07(1H,dd), 4.23(1H,q,J=7.5Hz), 5.00(1H,d,J=7.5Hz), 5.88(1H,d,J=2.5Hz), 8.18(1H,d,J=7.5Hz) Mass spec (Low resolution) :MH$^+$=300 Mass analysis C$_{13}$H$_{21}$N$_3$O$_5$. 1.2 C$_2$HF$_3$O$_2$. Required: C, 42,41; H, 5.13; N, 9.63. Found: C, 42.33; H, 5.25; N, 9.66.

EXAMPLE 14

(4S,5R,6R)-5-Acetylamino-4-amino-6-(ethylpropylcarbamoyl)-5,6-dihydro-4H-pyran-2-carboxylic acid trifluoroacetate salt $^1$H NMR (D$_6$-DMSO,250MHz)0.83(3H,m), 1.00(1H,t,J=7.5Hz), 1.15(2H,t,J=7.5Hz), 1.40–1.63(2H,m), 1.80(3H,s), 3.00–3.60(4H,m), 4.08(1H,m), 4.23(1H,m,J=7.5Hz), 5.00 (1H,t,J=7.5Hz), 5.87(1H,t), 8.18(1H,m) Mass analysis C$_{16}$H$_{24}$F$_3$N$_3$O$_7$. H$_2$O. Required: C, 43.15; H, 5.88; N, 9.43. Found: C, 43.41; H, 5.73; N, 9.22.

EXAMPLE 15

(4S,5R,6R)-5-Acetylamino-4-amino-6-[(3-phenylpropyl)propylcarbamoyl]-5,6-dihydro-4H-pyran-2-carboxylic acid trifluoroacetate salt $^1$H NMR (250MHz, D$_2$O, rotamers) 7.3(5H, m), 6.00+5.85 (1H, 2×d), 5.25+4.5+4.2+4.1 (3H, m), 3.7–3.1 (4H, m), 2.6 (2H, m), 2.2–1.5 (4H, m), 2.0 (3H, s), 0.9 (3H, 2×t)

Mass analysis C$_{23}$H$_{30}$F$_3$N$_3$O$_7$. H$_2$O. Required: C, 51.6; H, 6.0; N, 7.85. Found: C, 51.86; H, 5.84; N, 7.78.

EXAMPLE 16
(4S,5R,6R)-5-Acetylamino-4-amino-6-[nonylpropylcarbamoyl]-5,6-dihydro-4H-pyran-2-carboxylic acid trifluoroacetate salt $^1$H NMR (250MHz, $D_6$-DMSO+TFA) 8.15–8.35 (3H,m), 5.92 (1H,d), 5.04 (1H,d), 4.27 (1H,q), 4.13 (1H,broad s), 3.47 (2H,m), 2.95–3.30 (2H,m), 1.83 (3H,s), 1.40–1.70 (4H,m), 1.25(12H,s), 0.85 (6H,m). Mass analysis $C_{23}H_{38}F_3N_3O_7$. $0.5H_2O$ Required: C, 51.68; H, 7.35; N, 7.86. Found: C, 51,84; $H_{7.45}$; N, 7.80

EXAMPLE 17
(4S,5R,6R)-5-Acetylamino-4-amino-6-(cyclopropylmethylpropylcarbamoyl)-5,6-dihydro-4H-pyran-2-carboxylic acid trifluoroacetate salt $^1$H NMR (250MHz, $D_2O$, rotamers) 6.01 (1H, d, J=2.5Hz), 5.24 (1H, t, J=9.5Hz), 4.51 (1H, t, J=9.5Hz), 4.35—4.25 (1H, m), 3.70—2.95 (4H, m), 2.02+1.99(3H, 2xs), 1.75—1.50 (2H, m), 1.1—0.9(1H, m), 0.9—0.8(3H, 2xt), 0.65—0.45 (2H, m), 0.4–0.15 (2H, m). Mass spec (Low resolution): MH$^+$=340 Mass analysis $C_{18}H_{26}F_3N_3O_7$. $0.5H_2O$. Required: C, 46.75; H, 5.84; N, 9.09. Found: C, 46.80; H, 5.84; N, 9.19.

EXAMPLE 18
(4S,5R,6R)-5-Acetylamino-4-amino-6-(2-(2-pyridyl)ethylmethylcarboxamoyl)-5,6-dihydro-4H-pyran-2-carboxylic acid $^1$H NMR ($D_2O$): rotamers 8.65 (1H, m), 8.5 (1H, m), 7.92 (2H, m), 5.95 (1H, d), 5.19 (1H, d), 4.4 (1H, t), 4.20—4.0 (2H, m), 3.7—3.5 (1H, m), 3.35 (2H, m), 3.25+3.0 (3H, s), 2.0(3H, s); Mass spec (Low resolution): MH$^+$=363; Mass analysis $C_{17}H_{22}N_4O_5.2C_2HF_3O_2$. Required: C 42.72; H 4.10; N 9.49. Found: C 42.90; H4.25; N8.94.

EXAMPLE 19
(4S,5R,6R)-5-Acetylamino-4-amino-6-ethoxy(propyl)carboxamoyl-5,6-dihydro-4H-pyran-2-carboxylic acid $^1$H NMR ($D_2O$): rotamers 5.95 (1H, M), 5.23 (1H, d, J=10Hz), 4.50 (1H, t, J=10Hz), 4.29 (1H, dd, J=2.5,10Hz), 4.22—3.71 (3H, m), 3.58—3.42 (1H, m), 2.02 (3H, s), 1.80—1.49 (2H, M), 1.24 (3H, t, J=7Hz), 0.88 (3H, t, J=7.5Hz); Mass spec (Low resolution): MH$^+$=330. Mass analysis $C_{16}H_{24}F_3N_3O_8$. Required: C43.34; H 5.46; N 9.48. Found: C 42.10; H 5.55; N9.42.

EXAMPLE 20
(4S,5R,6R)-5-Acetylamino-4-amino-6-[phenethylpropylcarbamoyl]-5,6-dihydro-4-H-pyran-2-carboxylic acid trifluoroacetate salt $^1$H NMR (250MHz, $D_6$-DMSO+TFA, rotamers) 8.20 (1H, m), 7.10—7.45 (6H,m), 5.86 (1H,s), 4.99 (1H,m), 4.25 (1H,m), 4.05 (1H,m), 3.10–3.80 (4H,m), 2.70—3.00 (2H, dm), 2.08 (2H,s), 1.82(3H,d), 0.90–1.20 (3H,dm). Mass analysis $C_{21}H_{26}F_3N_3O_7$. 0 $.5H_2O$ Required: C, 50.60; H, 5.46; N, 8.43. Found: C, 50.54; H, 5.45N, 8.33.

EXAMPLE 21
(4S,5R,6R)-5-Acetylamino-4-amino-6-[hydroxyethylpropylcarbamoyl]-5,6-dihydro-4H-pyran-2-carboxylic acid trifluoroacetate salt $^1$H NMR (250MHz, $D_6$-DMSO+TFA, rotamers) 8.10–8.65 (4H,m), 6.04 (1H,d), 4.95–5.20 (1H,2xd), 4.60–4.70 (1H, m), 4.00–4.60 (2H,m), 3.05–3.70 (4H,m), 2.95 (1H,m), 1.90 (3H,d), 1.60–1.75 (2H,m), 1.25–1.5 (3H,d of t). Mass analysis $C_{14}H_{23}N_3O_6$. $1.5 C_2HF_3O_2$. $0.5H_2O$. Required: C, 40.08; H, 5.05; N, 8.25. Found: C, 40.03; H, 4.90; N, 8.09.

EXAMPLE 22
(4S,5R,6R)-5-Acetylamino-4-amino-6-(2-(2-thienyl)ethylcarboxamoyl)-5,6-dihydro-4H-pyran-2-carboxylic acid $^1$H NMR (250MHz $D_2O$): 7.3 (1H, d), 7.0 (1H, m), 6.93 (1H, d), 5.93 (1H, d), 4.45 (1H, d), 4.41 (1H, t), 4.42 (1H, dd), 3.65—3.4 (2H, m), 3.05 (2H, t), 2.0 (3H, s); Mass spec (Low resolution): MH$^+$=354; Mass analysis $C_{17}H_{22}N_4O_5.2C_2HF_3O_2.0.75H_2O$. Required: C, 42.46; H, 4.51; N, 8.74; S, 6.7; Found: C, 42.55; H, 4.65; N, 9.17; S, 6.9.

EXAMPLE 23
(4S,5R,6R)-5-Acetylamino-4-amino-6-[diallylcarbamoyl]-5,6-dihydro-4H-pyran-2-carboxylic acid trifluoroacetate salt $^1$H NMR (250MHz, $D_6$—MDSO+TFA) 8.25 (4H,m), 5.60–6.00 (3H,m), 5.00–5.30 (5H,m), 3.65–4.40 (6H,m), 1.83 (3H,s). Mass analysis $C_{17}H_{22}F_3N_3O_7$. $0.75H_2O$. Required: C, 45.29; H, 5.25; N, 9.32. Found: C, 45.39; H, 5.36; N, 9.33.

EXAMPLE 24
(4S,5R,6R)-5-Acetylamino-4-amino-6-(phenethylisobutylcarbamoyl)-5,6-dihydro-4H-pyran-2-carboxylic acid trifluoroacetate salt $^1$H NMR (250 MHz, $D_2O$, rotamers) 7.2–7.45 (5H, m), 5.96+5.85 (1H, 2xd), 5.20 (1H, d, J=9Hz), 4.63 (1H, t, J=8Hz), 4.40 (1H, d, J=7Hz), 4.23 (1H, dd, J=7, 3Hz), 4.16 (1H, t, J=7,5Hz), 4.07 (1H, dd, J=7, 3Hz), 3.91—3.55 (1H, m), 3.37 (1H, dd, J=15, 7Hz), 3.17 (1H, m), 3.06 (1H, dd, J=15, 7Hz), 2.96 (1H, t, J=7.5Hz), 2.01+1.98(3H,2xs), 0.95—0.80 (6H,m). Mass spec (Low resolution): MH$^+$=404 Mass analysis $C_{23}H_{30}F_3N_3O_7$. $0.25H_2O$. Required: C, 52.92; H, 5.89; N, 8.05. Found: C, 52.87; H, 5.93; N, 7.92.

EXAMPLE 25
(4S,5R,6R)-5-Acetylamino-4-amino-6-[(2-naphthalen-1-ylethyl)propylcarbamoyl]-5,6-dihydro-4H-pyran-2-carboxylic acid trifluoroacetate salt $^1$H NMR (250MHz, $D_6$—DMSO, rotamers) 8.4—7.4 (8H, m), 5.85 (1H, 2xd), 5.05 (1H, 2xd), 4.4—3.0 (6H, m), 1.85+1.80 (3H, 2xs), 1.6—1.4 (4H, m), 0.85 (3H, 2xt). Mass spec (Low resolution): MH$^+$=440 Mass analysis $C_{24}H_{29}N_3O_5$. $0.9 C_2HF_3O_2$. Required: C, 57.16; H, 5.56; N, 7.75. Found: C, 57.1; H, 5.8; N, 7.55.

EXAMPLE 26
(4S,5R,6R)-5-Acetylamino-4-amino-6-(N,N'-diethylhydrazinocarbonyl)-5,6-dihydro-4H-pyran-2-carboxylic acid trifluoroacetate salt $^1$H NMR (250MHz, $D_6$—DMSO) 8.0 (1H, d, J=7.5Hz), 5.8 (1H, d), 5.5 (1H, d, J=9Hz), 5.05 (1H, br t), 4.25 (1H, q), 4.1 (1H, dd), 3.5 (2H, m), 2.8 (3H, m), 1.8 (3H,s), 1.1(3H, t), 1.0 (3H, t) Mass spec (Low resolution): MH$^+$=315 Mass analysis $C_{13}H_{22}N_4O_5$. $1.15 C_2HF_3O_2$. Required: C, 41.25; H, 5.24; N, 12.58. Found: C, 41.0; H, 5.7; N, 12.3

EXAMPLE 27
(4S,5R,6R)-5-Acetylamino-4-amino-6-[hydroxyethylphenethylcarbamoyl]-5,6-dihydro-4H-pyran-2-carboxylic acid trifluoroacetate salt $^1$H NMR (250MHz, $D_6$—DMSO+TFA, rotamers) 8.25 (4H, m), 7.10–7.50 (6H,m), 5.93 (1H,s,), 4.90–5.20 (1H,m), 4.00–4.60 (3H,m), 3.10–3.90 (5H,m), 2.95 (1H,m), 2.75 (1H,m), 1.85 (3H,m). Mass analysis $C_{21}H_{26}F_3N_3O_8$. 0. $5H_2O$ Required: C, 49.03; H, 5.29; N 8.17. Found: C, 49.04; H, 4.91; N, 7.45.

EXAMPLE 28
(4S,5R,6R)-5-Acetylamino-4-amino-6-[ethylisopropylcarbamoyl]-5,6-dihydro-4H-pyran-2-carboxylic acid trifluoroacetate salt $^1$H NMR (250 MHz, $D_6$—DMSO); 5.99 (1H, m), 5.30, 5.13 (1H, 2d, J=8 Hz), 4.80—4.00 (3H, m), 3.42, (1H, m)3.27

(1H,m), 2.01 (3H, s), 1.30—1.03 (9H, m); Mass spec (Low resolution): MH⁺314; Mass analysis $C_{16}H_{24}F_3N_3O_7$. 0.4 $H_2O$) Required: C, 44.22; H, 5.75; N, 9.67. Found: C, 44.17; H, 6.00; N, 9.56.

EXAMPLE 29

(4S,5R,6R)-5-Acetylamino-4-amino-6-{[2-(4-methoxyphenyl)ethyl] propylcarbamoyl}-5,6-dihydro-4H-pyran-2-carboxylic acid trifluoroacetate salt ¹H NMR (250MHz, $D_6$—DMSO, rotamers) 8.20 (1H, 2×d, J=8.7Hz), 7.18 (2H, 2×d), 6.86 (2H, d, J=8Hz), 5.84 (1H, s), 4.99 (1H, t, J=8Hz), 4.20+4.04 (2H, 2×m), 3.72 (3H,s), 3.1—2.6 (6H,m), 1.82+1.80 (3H, 2×s), 1.6—1.4 (2H, m), 0.81 (3H, 2×t, J=6Hz) Mass spec (Low resolution): MH⁺= 420 Mass analysis $C_{23}H_{30}F_3N_3O_8$ Required: C, 51.78; H, 5.67; N, 7.88. Found: C,51.69; H, 5.93; N,7.90.

EXAMPLE 30

(4S,5R,6R)-5-Acetylamino-4-amino-6-{[2-(4-hydroxyphenyl)ethyl] propylcarbamoyl}-5,6-dihydro-4H-pyran-2-carboxylic acid trifluoroacetate salt ¹H NMR (250MHz, $D_6$—DMSO, rotamers) 9.22 (1H, br s), 8.20 (1H, m), 7.04 (2H, m), 6.68 (2H, d, J=7.5Hz), 5.87 (1H, br s), 5.01 (1H, d, J=8.5Hz), 4.22+4.06 (2H, 2×m), 3.1—2.6 (6H, m), 1.82+1.80 (3H, 2×s), 1.65—1.0 (2H, m), 0.8 (3H, m). Mass spec (Low resolution): MH⁺=406 Mass analysis $C_{22}H_{28}F_3N_3O_8$. Required: C, 50.87; H, 5.78; N, 8.09. Found: C, 50.61; H, 5.93; N, 7.90

EXAMPLE 31

(4S,5R,6R)-5-Acetylamino-4-amino-6[(2-biphenyl-4-yl-ethyl)carbamoyl]-5,6-dihydro-4H-pyran-2-carboxylic acid trifluoroacetate salt ¹H NMR (250MHz, $D_6$—DMSO rotamers) 8.24 (1H, br), 7.70—7.55 (9H, m), 5.91 (1H, m), 5.06 (1H, t), 4.31 (1H, m), 4.21 (1H, m), 3.8—2.8 (6H, m), 1.84+1.81 (3H, 2×s), 1.6—1.4 (2H, m), 0.81 (3H, m). Mass spec (Low resolution): MH⁺=466 Mass analysis $C_{28}H_{32}F_3N_3O_7$. $H_2O$. Required: C, 56.28: H, 5.73; N, 7.03. Found: C, 56.43; H, 5.57; N, 6.81

EXAMPLE 32

(4S,5R,6R)-5-Acetylamino-4-amino-6-{[2-(2,4-dichlorophenyl)ethyl] propylcarbamoyl}-5,6-dihydro-4H-pyran-2-carboxylic acid trifluoroacetate salt ¹H NMR (250MHz, $D_6$—DMSO rotamers) 8.21 (1H, m), 7.61—7.33 (3H, m), 5.81 (1H, s), 5.06+4.99 (1H, 2×d, J=8.5Hz), 4.19 (1H, m), 4.03 (1H, m), 3.73—2.73 (6H, m), 1.81+1.79 (3H, 2×s), 1.61—1.40 (2H, m), 0.81 (3H, m). Mass spec (Low resolution): MH⁺=458 Mass analysis $C_{22}H_{26}Cl_2F_3N_3O_7$ Required: C, 46.17: H, 4.58; Cl, 12.39; N, 7.34. Found: C, 46.85; H, 4.93; Cl, 12.6; N, 7.10

EXAMPLE 33

(4S,5R,6R)-5-Acetylamino-4-amino-6-{[2-(4-benzylphenyl)ethyl] propylcarbamoyl}-5,6-dihydro-4H-pyran-2-carboxylic acid trifluoroacetate salt ¹H NMR (250MHz, $D_6$—DMSO rotamers) 8.30—8.15 (4H, m), 7.30—7.11 (9H, m), 5.89 (1H, s), 5.01 (1H, 2×t), 4.24—4.09 (2H, m), 3.90 (2H, s), 3.7—2.4 (6H, m), 1.82+1.80 (3H, 2×s), 1.60—1.38 (2H, m), 0.78 (3H, 2×t). Mass spec (Low resolution): MH³⁰=480 Mass analysis $C_{29}H_{34}F_3N_3O_7$. 1.1 $H_2O$ Required: C, 56.78; H, 5.95; N, 6.85. Found: C, 56.61; H, 6.04; N, 6.89

EXAMPLE 34

(4S,5R,6R)-5-Acetylamino-4-amino-6-[(2-cyclohexylethyl)propylcarbamoyl]-5,6-dihydro-4H-pyran-2-carboxylic acid trifluoroacetate salt ¹H NMR (250MHz, $D_6$—DMSO 8.20 (1H, 2×d); 5.81 (1H, br s), 4.97 (1H, t, J=7Hz), 4.25—4.0 (2H, m), 3.5—3.0(4H, m), 1.80 (3H, s), 1.7—0.7 (18H, m). Mass spec (Low resolution): MH⁺=396 Mass analysis $C_{22}H_{34}F_3N_3O_7$. 0.25$H_2O$. Required: C, 51.41; H, 6.77; N, 8.15. Found: C, 51.44; H, 6.78; N, 8.15

EXAMPLE 35

(4S,5R,6R)-5-Acetylamino-4-amino-6-[(2-naphthalen-2-yl-ethyl)propylcarbamoyl]-5,6-dihydro-4H-pyran-2-carboxylic acid trifluoroacetate salt ¹H NMR (250MHz, $D_6$—DMSO rotamers) 8.26 (1H, m), 7.9—7.74(4H, m), 7.54—7.38 (3H, m), 5.88+5.84 (1H, 2×d), 5.08+5.02 (1H, 2×d), 4.25 (1H, m), 4.08 (1H, m), 3.8—2.8 (6H+$H_2O$, m), 1.82+1.80 (3H, 2×s), 1.65—1.40 (2H, m), 0.81 (3H, m). Mass spec (Low resolution): MH⁺= 440 Mass analysis $C_{26}H_{30}F_3N_3O_7$. 0.8$H_2O$. Required C, 57.94; H, 5.66; N, 7.92. Found: C, 57.88; H, 5.78; N, 7.63

EXAMPLE 36

(4R,5R,6R)-5-Acetylamino-4-amino-6-(2-phenethylcyclopropylcarbamoyl)-5,6-dihydro-4H-pyran-2-carboxylic acid ¹H NMR ($D_2O$): rotamers d 7.45 (5H, m), 5.76+5.62 (1H, d, J=3Hz), 5.55+4.30 (1H, d, J=8Hz), 4.51+4.12 (1H, t, J=8Hz), 4.16+4.05 (1H, dd, J=3, 8Hz), 3.82 (1H, m), 3.56 (1H, m), 3.05 (1H, m), 2.95 (2H, m), 2.05+1.85 (3H, s), 1.06+0.72 (4H, m); Mass spec (Low resolution): MH⁺=388; Mass analysis $C_{20}H_{25}N_3O_5.C_2HF_3O_2$. Required: C 52.81; H 5.73; N 8.38. Found: C 52.54; H 5.41; N9.19.

EXAMPLE 37

(4S,5R,6R)-5-Acetylamino-6-[nonylpropylcarbamoyl]-4-quanidino-5,6-dihydro-4H-pyran-2-carboxylic acid trifluoroacetate salt ¹H NMR (250MHz, $D_6$-DMSO+TFA) 8.82 (1H,m), 7.30—7.70 (3H,m), 6.02 (1H,d), 5.32 (1H,d), 4.10–4.40 (2H,2×m), 3.10–3.70 (5H,m), 2.05 (3H,s), 1.55–1.80 (4H,m), 1.41 (12H,s), 1.02 (6H,m). Mass analysis $C_{22}H_{39}N_5O_5$. 1.1 $C_2HF_3O_2$ Required: C, 50.20; H, 6.98; N 12.10. Found: C, 50.09; H, 6.77; N, 12.08.

EXAMPLE 38

(4S,5R,6R)-5-Acetylamino-6-[(2-cyclohexylethyl)propylcarbamoyl]-4-quanidino-5,6-dihydro-4H-pyran-2-carboxylic acid trifluoroacetate salt ¹H NMR (250MHz, $D_6$-DMSO 8.66 (1H, m), 8.0—7.0 (4H, m), 5.82 (1H, d, J=2Hz), 5.15 (1H, d, J=2Hz), 4.19 (1H, m), 4.01 (1H, m), 1.89 (3H, s), 1.75—0.80 (17H, m). Mass spec (Low resolution): MH⁺=438 Mass analysis $C_{23}H_{36}F_3N_5O_7$. $H_2O$. Required: C, 48.6; H, 6.6; N, 12.3. Found: c, 48.5; H, 6.4; N, 11.8.

EXAMPLE 39

(4S,5R,6R)-5-Acetylamino-6-[(4-biphenyl)ethylpropylcarbamoyl]-4-quanidino-5,6-dihydro-4H-pyran-2-carboxylic acid trifluoroacetate salt ¹H NMR (250MHz, $D_6$-DMSO+TFA, rotamers) 8.74 (1H, m), 7.00—8.00 (13H,m), 5.90 (1H,m), 5.20 (1H,d of d), 4.00–4.30 (2H,m), 3.62 (1H,m), 2.70–3.50 (5H,m), 1.92 (3H,d), 1.60 (2H,m), 0.88 (3H,m). Mass analysis $C_{29}H_{38}F_3N_5O_7$. 0.75$H_2O$ Required: C, 54.84; H, 5.63; N 11.03. Found: C, 55.05; H, 5.53; N, 10.69.

EXAMPLE 40

(4S,5R,6R)-5-Acetylamino-6-dipropylcarbamoyl-4-quanidino-5,6-dihydro-4H-pyran-2-carboxylic acid trifluoroacetate salt To a suspension of (4S,5R,6R)-5-acetylamino-4-amino-6-(1R,2R,3-trihydroxy-propyl)-5,6-dihydro-4-pyran-2-carboxylic acid trihydrate (7.8 g) in methanol (60 ml) was added (tert-butoxycarbonyliminio)-pyrazol-1-yl-methyl-carbamic acid tert-butyl ester (7.05 g,) and triethylamine (4.18 ml). The reaction was stirred at 23° C. for 18 hours. Diethyl ether (200 ml) was added and the resultant solid was collected by filtration to give a white solid. This was suspended in a solution of diphenyldiazomethane in dichloomethane (48 ml of a 0.47 M solution), acidified using 2N hydochloric acid and stirred rapidly for 18 hours. The organic phase was separated and the solvent removed in vacuo to gie a purple foam. This was chromatographed over silica gel (Merck 9385, 80 g) using medium pressure (~4psi) and ethyl acetate as eluant. The required fractions were combined and the solvent removed in vacuo to give the title compound as a white foam. (11.1 g) $^1$H NMR (250 MHz, $D_6$-DMSO) 11.40 (1H, s), 8.28 (1H, d, J=7.5 Hz), 8.21 (1H, d, J=8Hz), 7.49—7.27 (10H, m), 6.88 (1H, s), 5.97 (1H, d, J=2.5Hz), 4.88 (1H, m), 4.68 (1H, d, J=6Hz), 4.36 (1H, t, J=6Hz), 4.25 (1H, m), 4.12 (1H, m), 3.69 (2H, m), 3.44 (2H, m), 1.87 (3H, s), 1.48 (9H, s), 1.42 (9H, s); Mass analysis: $C_{35}H_{46}N_4O_{11}$. $0.5C_4H_8O_2$. $0.3H_2O$. Required: C, 59.39; H, 6.82; N, 7.49. Found: C, 59.41; $H_{6.46}$; N, 7.43.

b) (2R,3R,4S))3-Acetylamino-4-[2,3-bis(tert-butoxycarbonyl)guanidino]-3,4-dihydro-2H-pyran-2,6-dicarboxylic acid 6-benzhydryl ester To a solution of (4S,5R,6R)-5-actylamino-4-[2,3-bis(tert-butoxycarbonyl)-guanidino]-6-(1R,2R,3-trihydroxypropyl)-5,6-dihydro-4H-pyran-2-carboxylic acid benzhydryl ester (9.19 g) in methanol/water (5:1 v/v, 120 ml) was added sodium periodate (6.38 g) and the reaction was stirred at 23° C. for 1.5 hours. The solid was removed by filtration and the filtrate was evaporated in vacuo to give a white solid. This was suspended in t-butanol (55 ml) and cyclohexene (7.7 ml). To this was added a solution of sodium chlorite (8.14 g) and potassium dihydrogen orthophosphate (8.14 g) in water (44 ml) and the reaction was stirred at 23° C. for 2 hours. The reaction was acidified and extracted using ethyl acetate. The combined organic extracts were dried over anhydrous magnesium sulphate and the solvent was removed in vacuo to give a tan foam. This was dissolved in diethyl ether and petroleum ether (40–60) was added the solid was collected by filtration to give the title compound as a white solid. (6.00 g) $^1$H NMR (250MHz, $D_6$-DMSO) 11.39 (1H, s), 8.27—8.17 (2H, m), 7.50—7.27 (10H, m), 6.96 (1H, s), 6.19 (1H, d, J=5Hz), 4.82 (1H, d, J=4Hz), 4.53 (1H, m), 4.43 (1H, m), 1.83 (3H, s), 1.47 (9H, s), 1.41 (9H, s); Mass analysis: $C_{33}H_{40}N_4O_{10}$. $0.75C_4H_8O_2$. Required: C, 60.16; H, 6.45; N, 7.79. Found: C, 58.95; H, 6.21; N, 7.80 Mass spec low resolution): MH$^+$=653.

c) (2R,3R,4S)-3-Acetylamino-4-[2,3-bis(tert-butoxycarbonyl)guanidino]-3,4-dihydro-2H-pyran-2,6-dicarboxylic acid 6-benzhydryl ester 2-(2,3,4,5,6-pentafluorophenyl)ester To a solution of (2R,3R,4S)-3-Acetylamino-4-[2,3-bis(tert-butoxycarbonyl)-guanidino]-3,4-dihydro-2H-pyran-2,6-dicarboxylic acid 6-benzhydryl ester (4.4 g) in dry dimethylformamide (10 ml) and pyridine (0.70 ml) was added pentafluorophenyl trifluoroacetate (1.27 ml) and the reaction was stirred at 23° C. for 1 hour. More pyridine (0.70 ml) and pentafluorophenyl trifluoroacetate (1.27 ml) was added and the reaction was stirred for a further 2 hours. The reaction mixture was diluted using ethyl acetate and washed consecutively using 1N hydrochloric acid, saturated sodium bicarbonate solution and brine. The organic phase was dried over anhydrous magnesium sulphate and the solvent was removed in vacuo to give the crude title compound as a tan foam, (8.11 g); $^1$H NMR (250MHz, $D_6$-DMSO) 9.97 (1H, broad s), 7.49—7.27 (11H, m), 6.91 (1H, s), 6.52 (1H, m), 4.93 (1H, m), 4.58 (1H, m), 4.47 (1H, m), 1.88 (3H,s), 1.42 (18H, s).

d) (4S,5R,6R)-5-Acetylamino-4-[2,3-bis(tert-butoxycarbonyl)guanidino]-6-dipropylcarbamoyl-5,6-dihydro-4H-pyran-2-carboxylic acid benzhydryl ester To a solution of (2R,3R,4S)-3-Acetylamino-4-[2,3-bis(tert-butoxycarbonyl)-guanidino]-3,4-dihydro-2H-pyran-2,6-dicarboxylic acid 6-benzhydryl ester 2-(2,3,4,5,6-pentafluoro-phenyl) ester (0.70 g) in dry tetrahydrofuran (5 ml) was added dipropylamine (0.141 g) and the reaction was stirred at 23° C. for 4 hours. The solvent was removed in vacuo and the residue was chromatographed on silica gel (Merck 9385, 50 g) using medium pressure (~4psi) and cyclohexane/ethyl acetate (1:1 v/v) as the eluant. The required fractions were combined and the solvent removed in vacuo to give the title compound as a pale yellow foam. (0.341 g). $^1$H NMR (250MHz, $D_6$-DMSO) 11.46 (1H, s), 8.27 (1H, d, J=6.25 Hz), 8.16 (1H, d, J=7.5Hz), 7.48—7.27 (10H, m), 6.97 (1H, s), 6.14 (1H, d, J=5Hz), 5.18 (1H, m), 4.67 (1H, m), 4.10 (1H, m), 3.61—3.24 (3H, m), 3.14 (1H, m), 1.84 (3H, s), 1.60—1.34 (4H, m), 1.46 (9H, s), 1.40 (9H, s), 0.85 (3H, t, J=7Hz), 0.74 (3H, t, J=7Hz); Mass Analysis; $C_{39}H_{53}N_5O_9$. $1.0C_6HF_5O$. Required: C, 58.75; H, 5.92; N, 7.61. Found C, 58.64; H, 5.75; N, 7.61.

e) (4S,5R,6R)-5-Acetylamino-6-dipropylcarbamoyl-4-guanidino-5,6-dihydro-4H-pyran-2-carboxylic acid trifluoroacetate salt (4S,5R,6R)-5-Acetylamino-4-[2,3-bis(tert-butoxycarbonyl)-guanidino]-6-dipropylcarbamoyl-5,6-dihydro-4H-pyran-2-carboxylic acid benzhydryl ester (0.32 g) was dissolved in dichloromethane (2 ml) and trifluoroacetic acid (2 ml) and left to stand at 23° C. for 2 hours. The solvent was removed in vacuo and the residue triturated with diethyl ether (20 ml). The resulting solid was collected by filtration and dried to give the title compound as an off-white solid. (0.158 g)
$^1$H NMR (250MHz, $D_2O$) 5.97 (1H, d, J=3.8Hz), 5.29 (1H, d, J=6.3Hz), 4.41 (1H, dd, J=3.8, 6.3Hz), 4.30 (1H, t, J=6.3Hz), 3.63—3.08 (4H, m), 1.99 (3H, s), 1.66—1.51 (4H, m), 0.9 (6H, m); Mass Spec (Low resolution):MH$^+$= 370:Mass analysis:$C_{18}H_{28}F_3N_5O_7$. Required: C, 44.72H, 5.84; N,14.49. Found: C, 44.72; H, 5.87; N, 13.99.

The following Examples 41–43 were similarly prepared using the method described in Example 40:

EXAMPLE 41

(4S,5R,6R)-5-Acetylamino-6-dibutylcarbamoyl-4-guanidino-5,6-dihydro-4H-pyran-2-carboxylic acid trifluoroacetate salt $^1$H NMR (250MHz, $D_2O$) 5.99 (1H, d, J=3.8Hz), 5.29 (1H, d, J=6.3Hz), 4.39 (1H, m), 4.28 (1H, m), 3.58—3.12 (4H, m), 2.00 (3H, s), 1.75—1.13 (8H, m), 0.89 (6H, m); Mass spec (Low resolution): MH$^+$=398 Mass analysis: $C_{20}H_{32}F_3N_5O_7$. Requires: C, 46.96; H, 6.31; N, 13.69. Found: C,46.26; H, 5.94; N, 13.26.

EXAMPLE 42

(4S,5R,6R)-5-Acetylamino-6-(phenethylpropylcarbamoyl)-4-quanidino-5,6-dihydro-4H-pyran-2-carboxylic acid trifluoroacetate salt $^1$H NMR (250MHz, $D_2O$) 7.5—7.2 (5H, m), 5.98+5.85 (1H, 2×d), 5.28 (1H, d, J=6.5Hz), 4.6—2.8 (10H, m), 2.00+1.97

(3H, 2xs), 1.6—1.45 (2H, m), 0.86 (3H, t, J=7.5Hz). Mass spec (Low resolution) MH$^+$=432; Mass analysis $C_{23}H_{30}F_3N_5O_7$. Requires: C, 50.64; H, 5.54; N, 12.84. Found: C, 50.01; H, 5.50; N, 12.10.

EXAMPLE 43

(4S,5R,6R)-5-Acetylamino-6-(decylmethylcarbamoyl)-4-quanidino-5,6-dihydro-4H-pyran-2-carboxylic acid trifluoroacetate salt $^1$H NMR (250 MHz, D$_6$-DMSO) 8.68+8.59 (1H, 2xd), 7.23 (1H, m), 5.81 (1H, d, J=2.5Hz), 5.19 (1H, m), 4.20—4.00 (2H, m), 3.40—3.12 (2H, m), 3.03+2.81 (3H, 2xs), 1.87 (3H, 2xs), 1.42 (2H, m), 1.24 (16H, m), 0.87 (3H, m); Mass analysis $C_{23}H_{38}F_3N_5O_7$. 0.33H$_2$O. Requires: C, 49.37; H, 6.96; N, 15.52. Found: C, 49.41; H, 6.88; N, 12.51.

EXAMPLE 44

(4R,5R,6R)-5-Acetylamino-4-amino-6-(dipropylcarbamoyl)-5,6-dihydro-4H-pyran-2-carboxylic acid a) (2R,3R,4R)-3-Acetylamino-4-azido-3,4-dihydro-2H-pyran-2,6-dicarboxylic acid, 6-methyl ester.

To a solution of (4R,5R,6R)-5-acetylamino-4-azido-6-(1R,2R,1,2,3-trihydroxy-propyl)-5,6-dihydro-4H-pyran-2-carboxylic acid, methyl ester (WO91/16320) (3.95 g) in methanol/water (3:1 v/v, 60 ml) was added sodium periodate (5.18 g). After stirring at 23° C. for 17 hours the mixture was filtered and the filtrate was evaporated to leave an orange liquid. The liquid was suspended in tert-butanol (80 ml) under nitrogen and a solution of potassium dihydrogen orthophosphate (8.04 g) and sodium chlorite (8.04 g) in water (40 ml) was added. The mixture was stirred for 1 hour at 23° C., then was cooled in ice and was decolourised by the addition of 20% sodium metabisulphite solution. The mixture was extracted with ethyl acetate (x3) and the combined organic extracts were dried over anhdrous magnesium sulphate and the solvent was evaporated in vacuo to leave the <u>title compound</u> as a brown solid (1.95 g). $^1$H NMR (250MHz, D$_6$—DMSO) 8.2 (1H, d, J=8Hz), 5.9 (1H, d, J=3Hz), 4.65 (2H, m), 4.3 (1H, t, J=3.5Hz), 3.8 (3H, s), 3.0–3.5 (1H, broad s), 1.9 (3H, s). Mass spec. (low resolution): MH$^+$=285.

b) (4R,5R,6R)-5-Acetylamino-4-azido-6-(dipropylcarbamoyl)-5,6-dihydro-4H-pyran-2-carboxylic acid, methyl ester.

To a stirred solution of (2R,3R,4R)-3-acetylamino-4-azido-3,4-dihydro-2H-pyran,2,6-dicarboxylic acid, 6-methyl ester (1.75 g) and pyridine (0.75 ml) in dry dimethylformamide (10 ml) under nitrogen was added pentafluorophenyl trifluoroacetate (1.15 ml). After 4 hours at 23° C. the reaction mixture was diluted with ethyl acetate (250 ml) and was washed with dilute hydrochloric acid (x3), saturated sodium bicarbonate solution (x3) and brine. The organic phase was dried over anhydrous magnesium sulphate and the solvent was removed in vacuo to afford a brown oil which was redissolved in dry tetrahydrofuran (13 ml). Dipropylamine (1.45 ml) was added and the reaction was left for 17 hours at 23° C. The reaction mixture was concentrated and was partitioned between ethyl acetate and dilute hydrochloric acid. The organic phase was separated, was washed with dilute hydrochloric acid (x2), saturated sodium bicarbonate solution (x3) and brine. The organic phase was dried over anhydrous magnesium sulphate and the solvent was removed in vacuo to afford a brown syrup. The syrup was chromatographed over silica (Merck 9385, 100 g) using medium pressure (ca 4 psi) and ethyl acetate/cyclohexane (3:2 v/v) as eluant. Appropriate fractions were combined and the solvent was evaporated in vacuo to give a yellow solid which was triturated with ether to afford the <u>title compound</u> as pale yellow crystals (0.567 g). $^1$H NMR (250MHz, D$_6$-DMSO) 8.15 (1H, d, J=8Hz), 5.95 (1H, d, J=4Hz), 4.9 (1H, d, J=6Hz), 4.4–4.6 (2H, m), 3.8 (3H, s), 3.0–3.5 (4H, m), 1.85 (3H, s), 1.3–1.7 (4H, m), 0.8+0.87 (6H, two t, J=8Hz). Mass spec. (low resolution): MH$^+$=368. Mass analysis: $C_{16}H_{25}N_5O_5$. 0.25$C_4H_8O_2$ Required: C, 52.39; H, 6.93; N, 17.98. Found: C, 52.43; H, 6.93; N, 17.83.

c) (4R,5R,6R)-5-Acetylamino-4-amino-6-(dipropylcarbamoyl)-5,6-dihydro-4H-pyran-2-carboxylic acid.

To a stirred solution of (4R,5R,6R)-5-acetylamino-4-azido-6-(dipropylcarbamoyl)-5,6-dihydro-4H-pyran-2-carboxylic acid, methyl ester (500 mg) in tetrahydrofuran (6 ml) under nitrogen was added triphenylphosphine (428 mg). After 3.5 hours at 23° C. water (1 ml) was added adn the solution was stirred for a further 21 hours. Triethylamine (1 ml) was added and stirring was continued for a further 7 hours after which the solvents were removed in vacuo. The resulting liquid was redissolved in ethyl acetate, was dried over anhydrous magnesium sulphate, and the solvent was evaporated in vacuo to leave a yellow solid. The solid was chromatographed over silica (Merck 9385, 45 g) using medium pressure (ca 4 psi) and chloroform/methanol (15:1, v/v) as eluant. Appropriate fractions were combined and the solvent was evaporated in vacuo to afford a white solid which was suspended in water (5 ml) containing triethylamine (2 ml) and was stirred at 50° C. for 1.5 hours. The solvents were removed in vacuo to afford the <u>title compound</u> as a white solid (171 mg). $^1$H NMR (250MHz, D$_6$-DMSO) 8.4 (1H, broad s), 5.7 (1H, d, J=1.5Hz), 5.1 (1H, d, J=4Hz), 4.4 (1H, broad s), 3.95 (1H, broad s), 2.95–3.86 (6H, m), 2.0 (3H, s), 1.6 (4H, m), 0.94+0.99 (6H, two t, J=7.5Hz). Mass spec. (low resolution): MH$^+$=328. Mass analysis: $C_{15}H_{25}N_3O_5$. 1.5 H$_2$O Required: C, 50.79; H, 7.90; N, 11.85. Found: C, 50.87; H, 8.04; N, 11.54.

EXAMPLE 45

(4R,5R,6R)-5-Acetylamino-4-hydroxy-6-(phenethylpropylcarbamoyl)-5,6-dihydro-4H-pyran-2-carboxylic acid a) (4R,5R,6R)-5-Acetylamino-4-(tert-butyldiphenyl-silanyloxy)-6-[(1S,2R)-1,2,3-triacetoxy-propyl]-5,6-dihydro-4H-pyran-2-carboxylic acid, methyl ester.

(4R,5R,6R)-5-Acetylamino-4-hydroxy-6-[(1S,2R)-1,2,3-triacetoxypropyl]-5,6-dihydro-4H-pyran-2-carboxylic acid, methyl ester (55.0 g) in anhydrous dimethylformamide (200 ml) was treated with imidazole (17.5 g), 4-dimethylaminopyridine (2.8 g) and tert-butyldiphenylsilyl chloride (66 ml) and the reaction stirred under nitrogen and heated at 60° for 26 hours. A further aliquot of imidazole (1.75 g) and tert-butylidiphenylsilyl chloride (6.6 ml) was added and the reaction mixture heated for a further 19 hours. The reaction mixture was allowed to cool, concentrated, diluted with water (500 ml) and extracted with ethyl acetate (x2). These extracts were washed with dilute hydrochloric acid and brine and dried over anhydrous magnesium sulphate. The organic phase was evaporated to give a brown oil (120 g). The foam was chromatographed over silica (Merck 9385, 1 Kg) using medium pressure (ca 4 psi) and ethyl acetate/cyclohexane (1:2 v/v) as the eluant. The required fractions were combined and the solvent removed in vacuo to give the <u>title compound</u> as a white foam (66.0 g). $^1$H NMR (250 MHz, CDCl$_3$) 7.34–7.66 (10H, m), 5.71 (1H, d), 5.63 (1H, d), 5.34–5.47 (2H, m), 4.75 (1H, m), 4.13–4.40 (4H, m), 3.76 (3H, s), 2.10 (3H, s), 2.07 (3H, s), 2.06 (3H, s), 1.74 (3H, s), 1.10 (9H, s). Mass Spec. (Low resolution): MH$^+$=670. Mass Analysis: $C_{34}H_{43}NO_{11}Si$. Requires: C, 60.97; H,6.47; N, 2.09. Found: C, 60.45; H, 6.39; N, 2.00.

b) (4R,5R,6R)-5-Acetylamino-4-(tert-butyldiphenylsilanyloxy)-6-[(1R,2R)-1,2,3-trihydroxypropyl]-5,6-dihydro-4H-pyran-2-carboxylic acid, methyl ester.

(4R,5R,6R)-5-Acetylamino-4-(tert-butyldiphenylsilanyloxy)-6-[(1R,2R,3-triacetoxypropyl]-5,6-dihydro-4H-pyran-2-carboxylic acid, methyl ester (66.2 g) in anhydrous methanol (1L) was treated with sodium methoxide (0.5 g) and the reaction stirred under nitrogen for 1.5 hours. The reaction was neutralised by the addition of Dowex-50W-X8 and the resin removed by filtration. The filtrate was evaporated to give the title compound (53.2 g); NMR $^1$H (250 MHz, CDCl$_3$). 7.34–7.72 (10H, m), 6.27 (1H, s), 5.74 (1H, d), 4.32 (1H, dd), 4.22 (1H, d), 4.08 (2H, m), 3.91 (2H, dq), 3.74 (3H, s), 3.64 (1H, s), 1.85 (3H, s), 1.11 (9H, s). Mass Spec. (Low resolution): MH$^+$=544. Mass Analysis: $C_{28}H_{37}NO_8Si$. 0.5$H_2O$ Requires: C, 60.44; H,6.93; N, 2.53. Found: C, 60.45; H, 6.87; N, 2.62.

c) (2R,3R,4R)-3-Acetylamino-4-(tert-butyldiphenylsilanyloxy)-3,4-dihydro-2H-pyran-2,6-dicarboxylic acid 6-methyl ester.

(4R,5R,6R)-5-Acetylamino-4-(tert-butyldiphenylsilanyloxy)-6-[(1R,2R)-1,2,3-trihydroxypropyl]-5,6-dihydro-4H-pyran-2-carboxylic acid methyl ester (53.2 g) in methanol-water (3:1, 400 ml) was treated with sodium periodate (44.0 g) and stirred at 23° C. for 24 hours. The reaction mixture was filtered and the filtrate evaporated to give a white foam. This foam was suspended in tert-butanol (700 ml) and sodium chlorite (71.64 g) and potassium dihydrogen othophosphate (71.6 g) in water (300 ml) added. The reaction mixture was stirred for 3 hours, cooled in ice and 20% sodium metabisulphite added to declourise the solution (1.5 L). This was extracted with ethyl acetate and these extracts were washed with brine, dried over magnesium sulphate and evaporated to give a yellow foam (53.5 g). This was triturated with ether and diisopropylether to give the title compound (43.37 g). $^1$H NMR (250 MHz, CDCl$_3$). 7.34–7.72 (11H, m), 6.04 (1H, d), 5.82 (1H, d), 4.36 (1H, m), 4.30 (1H, m), 3.74 (3H, s), 1.11 (9H, s). Mass Spec. (Low resolution): MH$^+$=498. Mass Analysis: $C_{26}H_{31}NO_7Si$. 1.0$H_2O$ Requires: C, 60.56H, 6.45; N, 2.71. Found: C, 60.97: H, 6.97; N, 2.45.

d) (4R,5S,6R)-5-Acetylamino-4-(tert-butyldiphenylsilanyloxy)-6-(phenethylpropylcarbamoyl)-5,6-dihydro-4H-pyran-2-carboxylic acid, methyl ester.

2-(1H-Benzotriazol-1-yl)-1,1,3,3-tetramethyluronium tetrafluoroborate (1.42 g) was added to a solution of (2R,3S,4R)-3-acetylamino-4-(tert-butyldiphenylsilanyloxy)-3,4-dihydro-2H-pyran-2,6-dicarboxylic acid, 6-methyl ester (2 g) and N,N-diisopropylethylamine (1.4 ml) in dimethylformamide (5 ml), under nitrogen. To this was added N-phenethylpropylamine (722 mg) and the reaction was stirred at 23° C. for 16 hours. The solvent was removed in vacuo and the residue was partitioned between water and ethyl acetate. The organic extracts were dried over anhydrous sodium sulphate and the solvent was removed in vacuo to give a fawn foam. The foam was chromatographed over silica (Merck 9385, 45 g) using medium pressure (ca 4 psi) and ethyl acetate/cyclohexane (1:2 v/v) as the eluant. The required fractions were combined and the solvent removed in vacuo to give the title compound as a white foam (1.1 g). $^1$H NMR (250 MHz, CDCl$_3$, rotamers) 7.6—7.1 (15H, m), 6.0+5.95 (1H, 2×m), 5.9—5.8 (1H, 2×d, J=6Hz), 5.2 (1H, 2×d, J=5Hz), 4.6 (1H, 2×d, J=3Hz), 4.0—3.7 (1H, m), 3.8 (3H, 2×s), 3.5—2.9 (4H, m), 2.8+2.5 (2H, 2×m), 2.0 (3H, 2×s), 1.5 —1.2 (2H, m), 1.1 (9H, s), 0.9+0.7 (3H, 2×t, J=7Hz).

e) (4R,5R,6R)-5-Acetylamino-4-hydroxy-6-(phenethylpropylcarbamoyl)-5,6-dihydro-4H-pyran-2-carboxylic acid, methyl ester.

To a stirred solution of (4R,5S,6R)-5-acetylamino-4-(tert-butyldiphenylsilanyloxy)-6-(phenethylpropylcarbamoyl)-5,6-dihydro-4H-pyran-2-carboxylic acid, methyl ester (7 g) in tetrahydrofuran (70 ml) was added tetra-n-butylammonium fluoride (12 ml of a 1M solution in tetrahydrofuran). After 4 hours at 23° C. the solvent was removed in vacuo and the residue was partitioned between brine and ethyl acetate. The organic extracts were dried over anhydrous sodium sulphate and the solvent was removed in vacuo to give an oil. This was chromatographed over silica (Merck 9385, 700 ml) using medium pressure (ca 4 psi) and dichloromethane/methanol (95:5 v/v) as eluant. The required fractions were combined and the solvent removed in vacuo to give the title compound as a pale yellow foam (3.98 g). $^1$H NMR (250MHz, CDCl$_3$, rotamers) 7.3 (5H,m), 6.2 (1H, 2×d, J=4Hz), 5.1+4.9 (1H,2×d, J=6Hz), 4.6+4.5 (1H, 2×m), 4.4—4.2 (1H,2× m), 3.8 (3H, 2×s), 3.7—3.3 (4H, m), 3.0+2.8 (2H, 2×m), 2.0 (3H, 2×s), 1.8—1.3 (2H, m), 0.9 (3H, m); Mass spec. (low resolution) MH$^+$=405.

f) (4R,5R,6R)-5-Acetylamino-4-hydroxy-6-(phenethylpropylcarbamoyl)-5,6-dihydro-4H-pyran-2-carboxylic acid.

(4R,5R,6R)-5-Acetylamino-4-hydroxy-6-(phenethylpropylcarbamoyl)-5,6-dihydro-4-H-pyran-2-carboxylic acid, methyl ester (300 mg) in triethylamine/water (1:2, 1.5 ml) was heated at 50° C. for 2 hours. Further triethylamine (1 ml) was added and the reaction heated for 2 hours. The reaction mixture was evaporated to dryness and co-evaporated with toluene (5 ml, ×3) and ether and dried to give the title compound (155 mg). $^1$H NMR (250MHz, D$_6$-DMSO, rotamers) 7.7 (1H, 2×d, J=9Hz), 7.2—7.4 (5H, m), 5.8 (1H, 2×d, J=5Hz), 4.8 (1H, 2×d, J=8Hz)), 4.2 (1H, m), 4.1 (1H, m), 3.0–3.8 (5H, m), 2.7—2.9 (2H, m) 1.8 (3H, two s) 1.4–1.6 (2H, m) 0.8 (3H, m). Mass Spec. (Low resolution): MH$^+$=391. Mass Analysis: $C_{20}H_{26}N_2O_6$.0.8 $C_6H_5N$, 1.0 $H_2O$ Requires: C, 60.9; H,8.2; N, 8.0. Found: C, 60.9; H, 8.0; N, 8.1.

EXAMPLE 46

(4R,5R,6R)-5-Acetylamino-4-hydroxy-6-[(2-biphenyl-4-yl-ethyl)propylcarbamoyl]-5,6-dihydro-4H-pyran-2-carboxylic acid $^1$H NMR (250 MHz, D$_6$-DMSO, rotamers). 7.28–7.72 (10H, m), 5.82+5.76 (1H, 2d), 4.80 (1H, m), 4.18 (1H, m), 4.11 (1H, m), 2.7–3.8 (7H, m), 1.86+1.80 (3H, two s) 1.4–1.7 (2H, m) 0.76–0.91(3H, m). Mass Spec. (Low resolution): MH$^+$=467. Mass Analysis: $C_{26}H_{30}N_2O_6$.0.5 $C_6H_{15}N$, 1.0 $H_2O$ Requires: C, 64.49; H, 7.37; N, 6.48. Found: C, 64.85; H, 7.37; N, 6.52.

EXAMPLE 47

(4R,5R,6R)-5-Acetylamino-4-hydroxy-6-(dipropylcarbamoyl)-5,6-dihydro-4H-pyran-2-carboxylic acid NMR $^1$H (250 MHz, D$_6$-DMSO). 7.61 (1H, d), 5.74 (1H, d), 4.76 (1H, d), 4.16 (1H,m), 4.08 (1H, m), 2.9–3.8 (4H, m), 1.83 (3H, s), 1.36–1.68 (4H,m), 0.84 (6H, m). Mass Spec. (Low resolution): MH$^+$=329. Mass Analysis: $C_{15}H_{24}N_2O_6$.0.8 $C_6H_{15}N$, 1.0 $H_2O$ Requires: C, 55.66; H,8.96; N, 9.18. Found: C, 55.65; H, 9.14; N,9.00.

EXAMPLE 48

(4R,5R,6R)-6[(2-Biphenyl-4-yl-ethyl)propylcarbamoyl]-4-hydroxy-5-(2,2,2-trifluoroacetylamino)-5,6-dihydro-4H-pyran-2-carboxylic acid a) (4R,5S,6R)-5-(Acetyl-tert-butoxycarbonylamino)-6-[(2-biphenyl-4-yl-ethyl)propylcarbamoyl]-4-(tert-butyldiphenylsilanyloxy)-5,6-dihydro-4H-pyran-2-carboxylic acid, methyl ester.

To a solution of (4R,5R,6R)-5-acetylamino-6-[(2-biphenyl-4-yl-ethyl)propylcarbamoyl]-4-(tert-butyldiphenylsilanyloxy)-5,6-dihydro-4H-pyran-2-carboxylic acid methyl ester (1.06 g) and 4-dimethylaminopyridine (0.12 g) in dioxane (10 ml) was added di-tert-butyl dicarbonate (0.53 g). The mixture was heated at 83° C. and further di-tert-butyl dicarbonate (0.76 g) was added portionwise over 4.5 hours. The reaction was cooled and partitioned between ethyl acetate (50 ml) and water (35 ml). The aqueous phase was further extracted with ethyl acetate (30 ml) and the combined organic extracts were washed with dilute citric acid (30 ml), dilute sodium bicarbonate (30 ml), dried over anhydrous magnesium sulphate and the solvent removed in vacuo to give a red gum. The gum was chromatographed over silica (Merck 7734, 130 g) with ethyl acetate/cyclohexane (1:2 v/v) as the eluant. The required fractions were combined and the solvent removed in vacuo to give the title compound as a pale yellow foam (1.05 g). $^1$H NMR (250 MHz, CDCl$_3$, rotamers) 7.87—7.20 (19H, m), 5.86+5.80 (1H, 2×broad d), 5.49+5.44(1H, 2×d, J=5Hz), 4.56 (2H, m), 3.9+3.65 (3H, 2×s), 3.98—2.74 (6H, m), 2.39+2.37 (3H,2×s), 1.83 (1H, m), 1.55 (1H, m), 1.45 (9H, s), 1.15—0.7 (12H, 2×t, J=7Hz and s).

b) (4R,5S,6R)-6-[(2-Biphenyl-4-yl-ethyl)propylcarbamoyl]-5-(tert-butoxycarbonylamino)-4-(tert-butyldiphenylsilanyloxy)-5,6-dihydro-4H-pyran-2-carboxylic acid, methyl ester.

To a solution of (4R,5S,6R)-5-(acethyl-tert-butoxycarbonylamino)-6-[(2-biphenyl-4-yl-ethyl)propylcarbamoyl]-4-(tert-butyldiphenylsilanyloxy)-5,6-dihydro-4H-pyran-2-carboxylic acid, methyl ester (3.9 g) in methanol (80 ml) was added sodium methoxide (0.47 g). The solution was stirred at 23° C. for 40 hours, neutralised by the addition of 0.5N citric acid, before being concentrated in vacuo to give a white residue which was partitioned between ethyl acetate (120 ml) and water (80 ml). The separated aqueous phase was further extracted with ethyl acetate (60 ml) and the combined organic extracts were dired over anhydrous magnesium suphate and concentrated in vacuo to give a yellow gum. This gum was chromatographed over silica (Merck 7734, 130 g) with ethyl acetate/cyclohexane (1:4 v/v) as the eluant. The required fractions were combined and the solvent removed in vacuo to give the title compound as a white foam (1.22 g). $^1$H NMR (250 MHz, D$_6$—DMSO, rotamers) 7.8—7.2(19H, m), 6.99+6.9 (1H, 2×d), 5.55+5.51 (1H, 2×m), 4.96 (1H, m), 4.51+4.44 (1H, 2×m), 3.96 (1H, m), 3.88—2.75 (9H, m), 1.66—1.18 (11H, m and s), 1.04 (9H, s), 0.85+0.75 (3H, two t, J=8Hz).

c) (4R,5S,6R)-5-Amino-6-[(2-biphenyl-4-ylethyl)propylcabamoyl]-4-(tert-butylidiphenylsilanyloxy)-5,6-dihydro-pyran-4H-pyran-2-carboxylic acid, methyl ester To a solution of (4R,5S,4R)-6-[(2-biphenyl-4-yl-ethyl)-propyl-carbamoyl]-5-(tert-butoxycarbonyl-amino)-4-(tert-butyl-diphenyl-silanyloxy)-5,6-dihydro-pyran-4H-pyran-2-carboxylic acid methyl ester (0.71 g) in dioxane (10 ml) was added a solution of hydrogen chloride in dioxane (5 ml of a 4M solution). The solution was stirred at 23° C. for 68 hours. The solvent was removed in vacuo and the residue was dissolved in ethyl acetate (50 ml) and washed with dilute sodium bicarbonate (30 ml). The organic phase was dried over anhydrous magnesium sulphate and the solvent removed in vacuo to give a pale yellow gum. This gum was chromatographed over silica (Merck 7734, 70 g) with ethyl acetate/cyclohexane (1:1 v/v) as the eluant. The required fractions wewre combined and the solvent removed in vacuo to give the title compound as an off-white foam (0.265 g). $^1$H NMR (250MHz, CDCl$_3$, rotamers) 7.78—7.27 (19H, m), 5.68+5.67 (1H, 2×d, J=5Hz), 4.69 (1H, d, J=9Hz), 4.42 (1H, dd, J=5Hz), 3.77—2.85 (10H, m), 1.5—1.8 (4H, m), 1.09 (3H, s), 0.93 (3H, 2×t, J=8Hz).

d) (4R,5S,6R)-6-[(2-Biphenyl-4-ylethyl)propylcarbamoyl]-4-(tert-butyldiphenylsilanyloxy)-5-(2,2,2,-trifluoroacetylamino)-5,6-dihydro-4H-pyran-2-carboxylic acid methyl ester.

To a solution of (4R,5S,6R)-5-amino-6-[(2-biphenyl-4-ylethyl)propylcarbamoyl]4-(tert-butyldiphenylsilanyloxy)-5,6-dihydro-pyran-4H-pyran-2-carboxylic acid methyl ester (1.02 g) in pyridine (13 ml) at 3° C. was added trifluoroacetic anhydride (0.25 ml). After 10 minutes at 3° C., the ice bath was removed and stirring was continued for 2 hours at 23° C. Ethyl acetate (50 ml) was added and the solution was washed with dilute hydrochloric acid (5×25 ml), brine (50 ml), dried over anhydrous magnesium sulphate and the solvent removed in vacuo to give a yellow gum (1.24 g). The gum was chromatographed over silica (Merck 7734, 70 g) with ethyl acetate/cyclohexane (1:4 v/v) as the eluant. The required fractions were combined and the solvent removed in vacuo to give the title compound as a white foam (0.83 g). $^1$H NMR (250 MHz, CDCl$_3$, rotamers) 7.7—7.16 (19H, m), 6.76 (1H, broad d), 5.98+5.93 (1H, 2×d, J=3Hz), 5.23+5.14 (1H,2×d, J=4Hz), 4.79 (1H, dd, J=6Hz, 3Hz), 3.83 (1H, m), 3.81+3.77 (3H, 2×s), 3.7—2.77 (4H, m), 2.63 (3H, t, J=9Hz), 1.6—1.3 (2H, m), 1.09 (9H, s), 0.89+0.79(3H, 2×t, J=8Hz).

e) (4R,5R,6R)-6-[(2-Biphenyl-4-ylethyl)propylcarbamoyl]-4-hydroxy-5-(2,2,2-trifluoroacetylamino)-5,6-dihydro-4-H-pyran-2-carboxylic acid, methyl ester.

To a solution of (4R,5R,6R)-6-[(2-biphenyl-4-yl-ethyl)propylcarbamoyl]-4-(tertbutyldiphenylsilanyloxy)-5-(2,2,2-trifluoroacetylamino)-5,6-dihydro-4-H-pyran-2-carboxylic acid methyl ester (1.03 g) in tetrahydrofuran (5.5 ml) was added a solution of tetra-n-butyl ammonium fluoride in tetrahydrofuran (1.45 ml of a 1M solution). The orange solution was stirred at room temperature for 4 hours before the solvent was removed in vacuo to give an orange gum. This was dissolved in ethyl acetate (50 ml) and washed with water (2×40ml). The organic phase was dried over anhydrous magnesium sulphate and the solvent was removed in vacuo and the residue was chromatographed over silica (Merck 7734, 65 g) and dichlormethane/methanol (95:5 v/v) as the eluant. The required fractions were combined and the solvent removed in vacuo to give the title compound as a white foam (0.64 g). $^1$H NMR (250 MHz, CDCl$_3$ rotamers) 7.63–7.24 (9H, m), 6.96+6.92 (1H, 2×d, J=8 Hz), 6.13+6.06 (1H, 2×d, J=4 Hz), 5.16+4.86 (1H, 2×d, J=7, 5 Hz), 4.72+4.58 (1H, 2×m), 4.3 (1H, m), 3.82+3.79 (3H, 2×s), 3.78–3.23 (4H, m), 3.02+2.87 (2H, 2×t, J=8 Hz), 2.90+2.78 (2H, 2×broad s), 1.82–1.50(2H, m), 0.96+0.92 (3H, 2×t, J=8 Hz).

f) (4R,5R,6R)-6-[(2-Biphenyl-4-ylethyl)propylcarbamoyl]-4-hydroxy-5-(2,2,2-trifluoroacetylamino)-5,6-dihydro-4H-pyran-2-carboxylic acid.

A mixture of (4R,5R,6R)-6-[(2-biphenyl-4-ylethyl) propylcarbamoyl]-4-hydroxy-5-(2,2,2-trifluoroacetylamino)-5,6-dihydro-4H-pyran-2-carboxylic acid methyl ester (0.63 g) in water (3 ml) and triethylamine (1.5 ml) was stirred at 50° C. for 5 hours. After cooling, the homogeneous solution was concentrated in vacuo to give a yellow gum. Azeotropic removal of the water in vacuo with dioxane (3×5 ml) produced a pale yellow foam (0.71 g). This foam was redissolved in a mixture of water (2 ml) and triethylamine (1 ml) before being stirred at 50° C. for a further 2 hours. After cooling the solvent was removed in vacuo and the residue was co-evaporated with dioxane (4×15 ml) and ether(3×15 ml) to give a yellow solid (0.62 g). This solid was purified by HPLC to give the title compound as a pink solid (0.24 g). $^1$H NMR (250 MHz, D$_6$-DMSO, rotamers) 13.2 (1H, broad s),9.32+9.28 (1H, 2×d, J=9 Hz), 7.7–7.17 (9H, m), 6.07+6.02 (1H, 2×d, J=5 Hz), 5.02+4.94 (1H, 2×d, J=9 Hz), 4.37+4.17 (2H, 2×m), 4.0–3.1 (4H, m), 3.02+2.77 (2H, 2×t, J=9 Hz), 1.66+1.47 (2H, 2×m), 0.86+0.81 (3H, 2×t, J=8 Hz); Mass spec (low resolution): MH=521; Mass Analysis: $C_{26}H_{27}F_3N_2O_6 \cdot H_2O$. Required: C, 58.0; H, 5.4; N, 5.2. Found: C, 57.6; H, 5.1; N, 4.9.

Example 49 was prepared in a similar manner to Example 48.

EXAMPLE 49

(4R,5R,6R)-6-[(2-Biphenyl-4-yl-ethyl)propylcarbamoyl]-4-hydroxy-5-propionylamino-5,6-dihydro-4-H-pyran-2-carboxylic acid $^1$H NMR (250 MHz, D$_6$-DMSO, rotamers) 7.7–7.3 (9H, m), 5.80+5.76 (1H, 2×d, J=5 Hz), 5.3 (1H, broad d), 4.78 (1H, 2×d, J=8 Hz), 4.22 (1H, m), 4.10 (1H, m), 3.9–2.8 (7H, m), 2.20–2.05 (2H, m), 1.47–1.40 (2H, m), 0.96+0.95 (3H, 2×t, J=8 Hz), 0.87+0.82 (3H, 2×t, J=8 Hz). Mass analysis: $C_{27}H_{32}F_3N_2O_6 \cdot 0.8 \, C_6H_{15}N \cdot 1.0 \, H_2O$. Required: C, 65.6; H, 7.9; N, 6.7. Found: C, 65.4; H, 7.5; N, 6.5.

EXAMPLE 50

(4S,5R,6R)-5-Acetylamino-4-hydroxy-6-[(2-biphenyl-4-yl-ethyl)propylcarbamoyl]-5,6-dihydro-4H-pyran-2-carboxylic acid a) (4S,5R,6R)-5-Acetylamino-4-(tert-butyldiphenylsilanyloxy)-6-[(1R,2R)-1,2,3-trihydroxypropyl]-5,6-dihydro-4H-pyran-2-carboxylic acid, methyl ester.

To a solution of (4S,5R,6R)-5-Acetylamino-6-[(S)-(2,2-dimethyl-[1,3]dioxolan-4R-yl)hydroxymethyl]-4-hydroxy-5,6-dihydro-4H-pyran-2-carboxylic acid, methyl ester (7.59 g), imidazole (3.04 g) and 4-dimethylaminopyridine (1.52 g) in dry dimethylformamide (100 ml) was added tert-butyl-diphenylsilylchloride (11.39 ml) and the reaction was heated at 70° C. for 48 hours. The reaction was cooled and the solvent was removed in vacuo. The residue was dissolved in ethyl acetate (300 ml) and then washed with dilute hydrochloric acid (100 ml), saturated sodium bicarbonate solution (100 ml) and brine (100 ml). The organic phase was dried over anhydrous magnesium sulphate and the solvent was removed in vacuo. The residue was dissolved in 80% acetic acid and was stirred at 23° C. for 24 hours. The solvent was then removed and the residue was co-evaporated with dioxane (2×100 ml). This was chromatographed over silica (Merck 9385, 500 g) using medium pressure (ca 4 psi) and cyclohexane/ethyl acetate (1:2 v/v) as the eluant. The required fractions were combined and the solvent removed in vacuo to give the title compound as a white foam. (9.85 g). $^1$H NMR (250 MHz, D$_6$-DMSO) 8.15 (1H, m), 7.62 (4H, m), 7.45 (6H, m), 5.47 (1H, d, J=3 Hz), 4.70 (1H, m), 4.59 (1H, d, J=4.5 Hz), 4.53 (1H, d, J=4.5 Hz), 4.35 (1H, t, J=4.5 Hz), 4.04 (2H, m), 3.62 (5H, m), 3.37 (2H, m), 1.85 (3H, s), 1.00 (9H, s).

b) (2R,3R,4S)-3-Acetylamino-4-(tert-butyldiphenylsilanyloxy)-3,4-dihydro-2H-pyran-2,6-dicarboxylic acid 6-methyl ester.

To a solution of (4S,5R,6R)-5-acetylamino-4-(tert-butyldiphenylsilanyloxy)-6-[(1R,2R)-1,2,3-trihydroxypropyl]-5,6-dihydro-4H-pyran-2-carboxylic acid, methyl ester, (9.0 g) in methanol/water (270 ml) was added sodium periodate (7.95 g) and the reaction was stirred at 23° C. for 1 hour. The suspension was filtered and the collected solid was washed with methanol (50 ml). The combined filtrates were evaporated in vacuo to give a white solid. The solid obtained was suspended in tert-butanol (110 ml) and stirred rapidly at 23° C. whilst a solution of potassium dihydrogen orthophosphate (12.4 g) and sodium chloride (12.4 g) in water (55 ml) was added. After 2 hours the mixture was cooled to 0° C. and dilute sodium metabisulphite solution was added until the reaction had become colourless. The reaction was diluted with water and then adjusted to pH 2 with dilute hydrochloric acid. The solution was extracted with ethyl acetate (3×500 ml) and the combined extracts were washed with brine (500 ml) and dried over anhydrous magnesium sulphate. The solvent was removed in vacuo to give the title compound as an off white foam (8.12 g). $^1$H NMR (250 MHz, D$_6$-DMSO) 7.93 (1H, d, J=9 Hz), 7.62 (4H, m), 7.42 (6H, m), 5.45 (1H, d, J=3 Hz), 4.85 (1H, s), 4.65 (1H, d, J=4.5 Hz), 3.78 (1H, m), 3.70 (3H, s), 1.85 (3H, s), 0.95 (9H, s).

c) (4S,5S,6R)-5-Acetylamino-4-(tert-butyldiphenylsilanyloxy)-6-[(2-biphenyl-4-yl-ethyl)propylcarbamoyl]-5,6-dihydro-4H-pyran-2-carboxylic acid methyl ester.

To a solution of (2R,3R,4S)-3-acetylamino-4-(tert-butyldiphenylsilanyloxy)-3,4-dihydro-2H-pyran-2,6-dicarboxylic acid, 6-methyl ester (2.0 g), (2-biphenyl-4-yl-ethyl)propylamine hydrochloride (1.33 g) and diisopropyl ethylamine (2.52 ml) in anhydrous dimethylformamide (5 ml) was added 2-(1H-benzotriazol-1-yl)-1,1,3,3-tetramethyl-uronium tetrafluoroborate (1.55 g). The reaction was stirred at 23° C. for 24 hours then diluted with ethyl acetate (200 ml) and washed with water (2×200 ml), dilute hydrochloric acid (100 ml), saturated sodium bicarbonate solution (100 ml) and brine (100 ml). The organic phase was dried over anhydrous magnesium sulphate and the solvent was removed in vacuo and the residue was chromatographed over silica (Merck 9385, 20 g) using medium pressure (ca 4 psi) and cyclohexane/ethyl acetate (10:1 v/v) as the eluant. The required fractions were combined and the solvent removed in vacuo to give the title compound as a white solid (1.6 g). $^1$H NMR (250 MHz, D$_6$-DMSO rotamers) 8.16+8.12 (1H,2×d, J=10 Hz), 7.64 (8H, m), 7.53–7.30 (11H, m), 5.50 (1H, m), 5.11 (1H, m), 4.54+4.40 (1H, 2×m), 4.26 (1H, m), 3.71+3.65 (3H, 2×s), 3.6–3.1 (4H, m), 2.92 (1H, m), 2.82 (1H, m), 1.81+1.79 (3H, 2×s), 1.62 (1H, m), 1.52 (1H, m), 1.02 (9H, s), 0.91+0.82 (3H, 2×t, J=7 Hz). Mass analysis: $C_{43}H_{50}N_2O_6Si$. Required: C, 71.84; H, 7.01; N, 3.90. Found: C, 71.54; H, 7.33; N, 3.88.

d) (4S,5R,6R)-5-Acetylamino-4-hydroxy-6-[(2-biphenyl-4-yl-ethyl)propylcarbamoyl]-5,6-dihydro-4H-pyran-2-carboxylic acid, methyl ester.

To a solution of (4S,5S,6R)-5-acetylamino-4-(tert-butyldiphenylsilanyloxy)-6-[(2-biphenyl-4-yl-ethyl)propylcarbamoyl]-5,6-dihydro-4H-pyran-2-carboxylic acid, methyl ester (1.58 g) in anhydrous tetrahydrofuran (15 ml) was added a solution of tetra-n-butylammonium fluoride in anhydrous tetrahydrofuran (2.42 ml of a 1N solution) and the reaction was stirred for 16 hours at 23° C. The solvent was then removed in vacuo and the residue was suspended in brine and extracted with ethyl acetate (3×50 ml). The combined organic extracts were dried over anhydrous magnesium sulphate and the solvent was removed in vacuo. The residue was chromatographed over silica (Merck 9385, 20 g) using medium pressure (ca 4 psi) and dichloromethane/methanol (95:5 v/v) as the eluant. The required fractions were combined and the solvent removed in vacuo to give the title compound as a white solid (0.91 g). $^1$H NMR (250 MHz, $D_6$-DMSO rotamers) 8.05 (1H, d, J=8 Hz), 7.63 (4H, m), 7.45 (2H, m), 7.34 (3H, m), 5.92+5.89 (1H, 2×d, J=3 Hz), 5.32 (1H, d, J=6 Hz), 5.01+4.97 (1H, 2×d, J=8 Hz), 4.28 (1H, m), 3.94 (1H, m), 3.73+3.68 (3H, 2×s), 3.45 (1H, m), 3.24 (1H, m), 2.96 (1H, m), 2.76 (1H, m), 1.82+1.79 (3H, 2×s), 1.57 (1H, m), 1.46 (1H, m), 0.83 (0.83(3H, m), Mass analysis: $C_{27}H_{32}N_2O_6$. Required: C, 67.48; H, 6.71; N, 5.83. Found: C, 67.08; H, 6.61; N, 5.60.

e) (4S,5R,6R)-5-Acetylamino-4-hydroxy-6-[(2-biphenyl-4-yl-ethyl)propylcarbamoyl]-5,6-dihydro-4H-pyran-2-carboxylic acid.

A mixture of (4S,5R,6R)-5-acetylamino-4-hydroxy-6-[(2-biphenyl-4-yl-ethyl)propylcarbamoyl]-5,6-dihydro-4H-pyran-2-carboxylic acid, methyl ester (0.89 g) water (5 ml) and triethylamine (5 ml) was heated at 50° C. for 6 hours. The solvent was then removed in vacuo and the residue was co-evaporated with dioxane (×3) to afford the title compound as an off white solid (0.87 g). $^1$H NMR (250 MHz, $D_6$-DMSO rotamers) 7.96 (1H, d, J=8 Hz), 7.60 (4H, m), 7.45 (2H, m), 7.33 (3H, m), 5.72 (1H, m), 5.15 (1H, m), 4.90 (1H, m), 4.25 (1H, m), 3.87 (1H, m), 3.60–2.95 (8H, m), 1.80+1.75 (3H, 2×s), 1.55 (1H, m), 1.46 (1H, m), 0.83 (3H, m). Mass analysis: $C_{26}H_{30}N_2O_6$. 1.0 $H_2O$. 0.6 $C_6H_{15}N$ Required: C, 65.20; H, 7.58; N, 6.68. Found: C, 65.40; H, 7.59; N, 6.44.

Example 51 was prepared in a similar manner to Example 50.

EXAMPLE 51

(4S,5R,6R)-5-Acetylamino-4-hydroxy-6-(phenethylpropylcarbamoyl)-5,6-dihydro-4H-pyran-2-carboxylic acid $^1$H NMR (250 MHz, $D_6$-DMSO rotamers) 8.00 (1H, d, J=8 Hz), 7.26 (5H, m), 5.72+5.69 (1H, 2×d, J=3 Hz), 5.15 (1H, broad s), 4.86 (1H, t, J=8 Hz), 4.26 (1H, m), 3.85 (1H, m), 3.70–2.80 (7H, m), 2.71 (1H, m), 1.55 (1H, m), 1.44 (1H, m), 0.82 (3H, m). Mass analysis: $C_{20}H_{26}N_2O_6$.2.0 $H_2O$. 0.75 $C_6H_{15}N$ Required: C, 58.58; H, 8.28; N, 7.67. Found: C, 58.66; H, 8.02; N, 7.37.

EXAMPLE 52

(4S,5R,6R)-5-Acetylamino-6-(dipropylcarbamoyl)-4-methylamino-5,6-dihydro-4H-pyran-2-carboxylic acid, trifluoroacetate salt a) (4S,5R,6R)-5-Acetylamino-6-(dipropylcarbamoyl)-4-(2,2,2-trifluoroacetylamino)-5,6-dihydro-4H-pyran-2-carboxylic acid, benzhydryl ester To a stirred cooled solution (ice/water) of (4S,5R,6R)-5-acetylamino-4-amino-6-(dipropylcarbamoyl)-5,6-dihydro-4H-pyran-2-carboxylic acid, benzhydryl ester (1.7 g) in anhydrous dichloromethane (15 ml) containing pyridine (0.84 ml) and 4-dimethylaminopyridine (0.042 g) was added trifluoroacetic anhydride (0.59 ml) dropwise. The reaction was stirred for 1 hour in the cooling bath and for a further 48 hours at 23° C. The solvent was removed in vacuo leaving a brown oil which was taken up in ethyl acetate (125 ml), washed with aqueous saturated sodium bicarbonate (2×100 ml), water (100 ml) and brine (100 ml). The organic phase was dried over anhydrous magnesium sulphate and solvent was removed in vacuo. The residue was chromatographed over silica (Merck 9385, 50 g) using medium pressure nitrogen (ca 5 psi) and chloroform and methanol (9:1 v/v) as eluant. The required fractions were combined and solvent was removed to give the title compound as a white solid (1.88 g). $^1$H NMR (250 MHz, $CDCl_3$) 8.79 (1H, d, J=8 Hz), 7.39–7.30 (10H, m), 7.00 (1H, s), 6.15 (1H, d, J=5 Hz), 5.75 (1H, d, J=8 Hz), 5.15 (1H, s), 4.55 (1H, dd, J=8 Hz, 6 Hz), 4.48 (1H, d, J=8 Hz), 3.49 (3H, s), 3.45–3.30 (2H, m), 3.30–3.10 (2H, m), 2.0 (3H, s), 1.68–1.52 (2H, m), 1.52–1.40 (2H, m), 1.92 (3H, t, J=8 Hz). Mass spec (Low Resolution): $MH^+$=590. Mass spec (High Resolution): $MH^+$=590.247788, fits for molecular formula $C_{30}H_{35}N_3O_6F_3$, error=0.0 ppm.

b) (4S,5R,6R)-5-Acetylamino-6-(dipropylcarbamoyl)-4-(2,2,2-trifluoroacetylmethylamino)-5,6-dihydro-4H-pyran-2-carboxylic acid, benzhydryl ester To a solution of 5-acetylamino-6-(dipropylcarbamoyl)-4-(2,2,2-trifluoroacetylamino-5,6-dihydro-4H-pyran-2-carboxylic acid, benzhydryl ester (0.133 g) in anhydrous dimethylformamide (2 ml) containing caesium carbonate (0.075 g) under a nitrogen atmosphere, was added iodomethane (0.144 g). The reaction was stirred at 23° C. for 144 hours then separated between water (10 ml) and ethyl acetate (30 ml). The organic phase was washed with water (20 ml), dried over anhydrous magnesium sulphate and the solvent was removed in vacuo. The residue was chromatographed over silica (Merck 9385, 9 g) using medium pressure nitrogen (ca 5 psi) and ethyl acetate/cyclohexane (2:1 v/v) as eluant. The required fractions were combined and solvent was removed in vacuo to give the title compound as a clear glass (0.116 g). $^1$H NMR (250 MHz, $CDCl_3$, rotamers) 7.95 (1H, d, J=9 Hz), 7.45–7.28 (10H, m), 6.91 (1H, s), 6.12 (1H, d, J=2.5 Hz), 5.46 (1H, dd, J=9 Hz, 2.5 Hz), 5.17 (1H, d, J=9 Hz), 3.60–3.40 (2H, m), 3.2–3.0 (3H, m), 2.97 (3H, s), 1.67 (3H, s), 1.60 (2H, m), 1.46 (2H, m), 0.84 (3H, t, J=7 Hz), 0.83 (3H, t, J=7 Hz), Mass spec (Low Resolution): $MH^+$=604. Mass spec (High Resolution): $MH^+$=604.263312, fits for molecular formula $C_{31}H_{37}N_3O_6F_3$, error=0.2 ppm.

c) (4S,5R,6R)-5-Acetylamino-6-(dipropylcarbamoyl)-4-methylamino-5,6-dihydro-4H-pyran-2-carboxylic acid, trifluoroacetate salt A solution of (4S,5R,6R)-5-acetylamino-6-(dipropylcarbamoyl)-4-(2,2,2-trifluoroacetylmethylamino)-5,6-dihydro-4H-pyran-2-carboxylic acid, benzhydryl ester (0.430 g) in dichloromethane (2.5 ml) and trifluoroacetic acid (2.5 ml) was stirred at 23° C. for 2 hours. The solvent was removed in vacuo and the residue was azeotroped with toluene (2×25 ml). The residue was taken up in a water/methanol mixture (20 ml, 1:1 v/v) and stirred at 23° C. with potassium carbonate (1.0 g) for 18 hours. The solvent was removed in vacuo and the residue was purified using HPLC on a reverse phase column eluted in a gradient procedure with water and acetonitrile containing trifluoroacetic acid. The required fractions were combined and solvent was removed in vacuo to give the title compound as a white solid (0.182 g). $^1$H NMR (250 MHz, $D_6$-DMSO,) 9.00 (2H, broad s), 8.35 (1H, d, J=8 Hz), 5.92 (1H, d, J=3 Hz), 5.05 (1H, d, J=8 Hz), 4.34 (1H, m), 3.46–3.30 (2H, m), 3.25–3.10 (1H, m), 3.08–2.90 (1H, m), 2.6 (3H, s), 1.75 (3H, s), 1.60–1.48 (2H, m), 1.48–1.30 (2H, m), 0.80 (3H, t, J=8 Hz), 0.75 (3H, t, J=8 Hz). Mass spec (Low Resolution): $MH^+$=342. Mass spec (High Resolution): $MH^+$=342.202998, fits for molecular formula $C_{16}H_{28}N_3O_5$, error=0.3 ppm.

EXAMPLE 53

(4S,5R,6R)-4-Amino-6-(dipropylcarbamoyl)-5-(2,2,2-trifluoroacetylamino)-5,6-dihydro-4H-pyran-2-carboxylic acid a) (2R,3R,4S)-4-Azido-3-(tert-butoxycarbonylamino)-3,4-dihydro-2H-pyran-2,6-dicarboxylic acid 6-methyl ester.

(4S,5R,6R)-4-Azido-5-(tert-butoxycarbonylamino)-6-[(1R,2R)-1,2,3-trihydroxypropyl]-5,6-dihydro-4H-pyran-2-carboxylic acid, methyl ester (3.88 g) in methanol/water (3:1; 100 ml v/v) was treated with sodium periodate (4.35 g) and stirred for 18 hours. The resulting suspension was filtered and the filtrate evaporated to dryness. The residue was suspended in tert-butanol (65 ml) and treated with a mixture of potassium dihydrogen orthophosphate (6.7 g) and sodium chlorite (6.7 g) in water (35 ml). After 3 hours the reaction was diluted with saturated sodium hydrogen carbonate and extracted with ethyl acetate. The aqueous liquors were acidified with dilute hydrochloric acid and extracted with ethyl acetate (×3). These extracts were washed with 10% sodium metabisulphite solution, dried with sodium sulphate and evaporated to give the title compound (3.1 g) NMR $^1$H (250 MHz, $D_6$-DMSO). 7.36 (1H, d, J=7.5 Hz), 5.96 (1H, d, J=4.0 Hz), 4.72 (1H, d, J=4.0 Hz), 4.22 (1H, m), 4.04 (1H, m), 3.76 (3H, s,), 1.38 (9H, s). $C_{13}H_{18}N_4O_7$. 0.25 $H_2O$ Requires: C, 45.0; H, 5.4; N, 16.2. Found: C, 44.9; H, 4.9; N, 15.7. Mass Spec. (Low Resolution): $MNH_4^+$=360.

b) (4S,5R,6R)-4-Azido-5-(tert-butoxycarbonylamino)-6-(dipropylcarbamoyl)-5,6-dihydro-4H-pyran-2-carboxylic acid, methyl ester.

(1,1,1-Benzotriazol-1-yl)-1,1,3,3-tetramethyluronium tetrafluoroborate (9.98 g) and dipropylamine (12.9 ml) were added to a stirred solution of (2R,3R,4S)-3-(tert-butoxycarbonylamino)-4-azido-3,4-dihydro-2H-pyran-2,6-carboxylic acid, 6-methyl ester (10.65 g) in anhydrous dimethylformamide (15 ml) cooled in a water bath. After 4 hours the mixture was partitioned between ethyl acetate and water. The organic phase was separated and was washed with water (×3) followed by saturated sodium bicarbonate solution (×3) and water. The organic phase was dried over anhydrous magnesium sulphate and the solvent was removed in vacuo to leave a brown foam (12.2 g). A portion of the foam (6.38 g) was chromatographed over silica (Merck 9385, 350 g) using medium pressure (ca 4 psi) and ethyl cyclohexane/acetate (5:1 v/v) as eluant. Appropriate fractions were combined and the solvent was evaporated in vacuo to afford a yellow solid which was triturated with diethyl ether to afford the title compound as a white solid (3.25 g). $^1$H NMR (250 MHz, $D_6$-DMSO): 7.26 (1H, d, J=9 Hz), 5.87 (1H, d, J=3 Hz), 4.9 (1H, d, J=9 Hz), 4.43 (1H, dd, J=8, 3 Hz), 3.8 (1H, q, J=8.5 Hz), 3.75 (3H, s), 3.4–3.6 (2H, m), 2.9–3.3 (2H, 2×m), 1.4–1.65 (4H, m), 1.35 (9H, s), 0.81+0.85 (6H, 2×t, J=7.5 Hz). Mass spec. (low resolution): $MH^+$=426. Mass analysis: $C_{19}H_{31}N_5O_6$ Required: C,53.64; H, 7.34; N, 16.46. Found: C, 53.77; H, 7.29; N, 16.48.

c) (4S,5R,6R)-5-Amido-4-azido-6-dipropylcarbamoyl-5,6-dihydro-4H-pyran-2-carboxylic acid, methyl ester hydrochloride.

To a stirred solution of (4S,5R,6R)-4-azido-5-(tert-butoxycarbonylamino)-6-dipropylcarbamoyl-5,6-dihydro-4H-pyran-2-carboxylic acid, methyl ester (2.26 g) in anhydrous tetrahydrofuran (17 ml) was added 4.0M hydrochloric acid in dioxane (27 ml). After 22 hours at 23° C. the solvent was evaporated and the residue was co-evaporated with dioxane (×3) and then cyclohexane to afford the title compound as a white solid (1.96 g). $^1$H NMR (250 MHz, $D_6$-DMSO) 8.75 (2H, broad s), 6.15 (1H, d, J=4 Hz), 5.45 (1H, d, J=4.5 Hz), 4.5 (1H, t, J=7.5 Hz). 3.75 (3H, s), 2.95–3.7 (5H, m), 1.4–1.65 (4H, m), 0.83+0.9 (6H, 2×t, J=7.5 Hz).

d) (4S,5R,6R)-4-Azido-6-(dipropylcarbamoyl)-5-(2,2,2-trifluoroacetylamino)-5,6-dihydro-4H-pyran-2-carboxylic acid, methyl ester.

To a solution of (4S,5R,6R)-5-amino-4-azido-6-(dipropylcarbamoyl)-5,6-dihydro-4H-pyran-2-carboxylic acid, methyl ester (2 g) in anhydrous pyridine (10 ml) at 0° C. was added trifluoroacetic anhydride (1.28 ml). The reaction was allowed to warm to 23° C., stirred for 2 hours and then diluted with ethyl acetate (30 ml). The solution was washed with dilute hydrochloric acid (20 ml), saturated sodium bicarbonate solution (20 ml) and brine (20 ml). The organic phase was dried over anhydrous magnesium sulphate, the solvent removed in vacuo and the residue was chromatographed over silica (Merck 9385, 50 g) using medium pressure (ca 4 psi) and cyclohexane/ethyl acetate (2:1 v/v) as the eluant. The required fractions were combined and the solvent removed in vacuo to give the title compound as a white solid (2.33 g). $^1$H NMR (250 MHz, $D_6$-DMSO) 9.75 (1H, d, J=6 Hz), 5.95 (1H, d, J=3 Hz), 5.05 (1H, d, J=9 Hz), 4.55 (1H, dd, J=3, 9 Hz), 4.25 (1H, m), 3.75 (3H, s), 3.45 (2H, m), 3.20 (1H, m), 2.95(1H, m), 1.55 (2H, m), 1.45 (2H, m), 0.85 (6H, m). Mass analysis: $C_{16}H_{22}F_3N_5O_5$. Required: C, 45.61; H, 5.26; N, 16.62. Found: C, 45.67; H, 5.22; N, 16.42.

e) (4S,5R,6R)-4-Amino-6-(dipropylcarbamoyl)-5-(2,2,2-trifluoroacetylamino)-5,6-dihydro-4H-pyran-2-carboxylic acid, methyl ester.

To a solution of (4S,5R,6R)-4-azido-6-(dipropylcarbamoyl)-5-(2,2,2-trifluoroacetylamino)-5,6-dihydro-4H-pyran-2-carboxylic acid, methyl ester (1 g) in dry tetrahydrofuran (10 ml) was added triphenylphosphine (0.75 g) and the reaction was stirred under nitrogen at 23° C. for 1.5 hours. To this was added water (2 ml) and triethylamine (2 ml) and the mixture was stirred for 16 hours at 23° C. The solvent was removed in vacuo and the residue was chromatographed over silica (Merck 9385, 50 g) using medium pressure (ca 4 psi) and dichloromethane/methanol (15:1 v/v) as the eluant. The required fractions were combined and the solvent removed in vacuo to give the title compound as a white solid. (0.87 g). $^1$H NMR (250 MHz, $D_6$-DMSO) 9.25 (1H, d, J=9 Hz), 5.90 (1H, d, J=3 Hz), 4.79 (1H, d, J=9 Hz), 4.00 (1H, m), 3.71 (3H, s), 3.58 (1H, m), 3.40 (2H, m), 3.16 (1H, m), 2.95 (1H, m), 1.84 (2H, s), 1.57 (2H, m), 1.40 (2H, m), 0.81 (6H, m), Mass analysis: $C_{16}H_{24}F_3N_3O_5$. 0.5 $H_2O$. Required: C, 47.52; H, 6.23; N, 10.39. Found: C, 47.68; H, 6.05; N, 10.10.

f) (4S,5R,6R)-4-Amino-6-(dipropylcarbamoyl)-5-(2,2,2-trifluoroacetylamino)-5,6-dihydro-4H-pyran-2-carboxylic acid.

A mixture of (4S,5R,6R)-4-amino-6-(dipropylcarbamoyl)-5-(2,2,2-trifluoroacetylamino)-5,6-dihydro-4H-pyran-2-carboxylic acid, methyl ester (0.34 g), triethylamine (1 ml) and water (2 ml) was heated at 50° C. for 2 hours. The solvent was removed in vacuo and the residue was co-evaporated with dioxane (×3) to afford the title compound as a white solid (330 mg). $^1$H NMR (250 MHz, $D_6$-DMSO) 9.40 (1H, s), 5.56 (1H, d, J=3 Hz), 4.70 (1H, d, J=9 Hz), 4.15 (1H, m), 3.85 (2H, m), 3.38 (2H, m), 3.15 (2H, m), 2.84 (2H, m), 1.47 (2H, m), 1.30 (2H, m), 0.72 (6H, m). Mass analysis: $C_{15}H_{22}F_3N_3O_5$. 1.25 $H_2O$. Required: C, 44.61; H, 6.11; N, 10.40. Found: C, 44.61; H, 6.10; N, 10.13.

Examples 54–57 were prepared in a similar manner to Example 53.

EXAMPLE 54

(4S,5R,6R)-4-Amino-6-(dipropylcarbamoyl)-5-propionylamino-5,6-dihydro-4H-pyran-2-carboxylic acid $^1$H NMR (250 MHz, $D_6$-DMSO) 8.10 (1H, d, J=9 Hz), 5.56 (1H, d, J=3 Hz), 4.92 (1H, d, J=9 Hz), 4.02 (1H, m), 3.90 (1H, m), 3.47 (1H, m), 3.14 (2H, m), 2.92 (2H, m), 2.05

(2H, m), 1.52 (2H, m), 1.45 (2H, m), 0.95 (3H, t, J=9 Hz), 0.82 (6H, m). Mass analysis: $C_{16}H_{27}N_3O_5$. 1.0 $H_2O$. Required: C, 53.47; H, 8.13; N, 11.69. Found: C, 53.37; H, 8.24; N, 11.69.

EXAMPLE 55

(4S,5R,6R)-4-Amino-6-(dipropylcarbamoyl)-5-methanesulphonylamino-5,6-dihydro-4H-pyran-2-carboxylic acid $^1$H NMR (250 MHz, $D_6$-DMSO) 5.56 (1H, d, J=3 Hz), 4.66 (1H, d, J=9 Hz), 4.15 (1H, m), 3.85 (2H, m), 3.38 (2H, m), 3.15 (2H, m), 2.84 (2H, m), 1.47 (2H, m), 1.30 (2H, m), 0.72 (6H, m). Mass analysis: $C_{14}H_{25}F_3N_3O_6S$. 0.75 $H_2O$. Required: C, 44.61; H, 7.09; N, 11.15; S, 8.51. Found C, 44.67; H, 7.25; N, 11.20; S, 8.27.

EXAMPLE 56

(4S,5R,6R)-4-Amino-6-(phenethylpropylcarbamoyl)-5-(2,2,2-trifluoroacetylamino)-5,6-dihydro-4H-pyran-2-carboxylic acid $^1$H NMR (250 MHz, $D_6$-DMSO rotamers) 9.50 (1H, m), 7.25 (5H, m), 5.69+5.67 (1H, 2×d, J=3 Hz), 4.83+4.78 (1H, 2×d, J=9 Hz), 4.25 (1H, t, J=9 Hz), 3.92 (1H, m), 3.65 (1H, m), 3.40 (1H, m), 3.21 (1H, m), 2.91 (2H, m), 2.68 (1H, m), 1.48 (1H, m), 1.40 (1H, m), 0.81 (3H, m). Mass analysis: $C_{20}H_{24}F_3N_3O_5$ 0.75 $H_2O$. Required: C, 52.57; H, 5.63; N, 9.20. Found: C, 52.74; H, 5.55; N, 9.19.

EXAMPLE 57

(4S,5R,6R)-4-Amino-6-(phenethylpropylcarbamoyl)-5-propionylamino-5,6-dihydro-4H-pyran-2-carboxylic acid $^1$H NMR (250 MHz, $D_6$-DMSO) 8.10 (1H, m), 7.25 (5H, m), 5.58 (1H, s), 4.90 (1H, m), 3.95 (2H, m), 3.7–2.90 (5H, m), 2.70 (1H, m), 2.09 (2H, m), 1.55 (1H, m), 1.45 (1H, m), 0.95 (3H, m), 0.81 (3H, m). Mass analysis: $C_{21}H_{29}N_3O_5$. 0.75 $H_2O$. Required: C, 60.49; H, 7.37; N, 10.08. Found C, 60.46; H, 7.59; N, 10.02.

We claim:

1. A compound of formula (I):

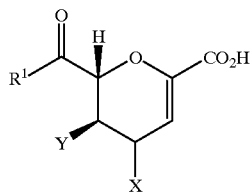

(I)

wherein
- $R^1$ represents $OR^5$, $SR^5$, $NR^5R^6$, $N(OR^5)R^6$ or $N(NR^5R^6)R^6$;
- X represents OH, $N_3$, $NR^3R^4$ or $NR^4CO_2R^{15}$;
- Y represents H or $NHR^2$;
- $R^2$ represents a group $SO_2R^7$ or $COR^7$;
- $R^3$ represents H, $C_{1-6}$ alkyl or $C(=NR^8)NR^9R^{10}$;
- $R^4$ represents H or $C_{1-6}$ alkyl;
- $R^5$ represents H, $C_{1-20}$ alkyl, $C_{3-8}$ cycloalkyl, $C_{2-20}$ alkenyl, $C_{2-20}$ alkynyl, $CHR^{11}COR^{12}$ or $C_{1-20}$ alkyl substituted by one or more groups selected from $NR^{13}R^{14}$, $NR^{13}COR^{14}$, $CO_2R^{13}$, $OR^{13}$, $C_{3-8}$ cycloalkyl, and optionally substituted aryl;
- each $R^6$ independently represents H, $C_{1-6}$ alkyl, $C_{3-8}$ cycloalkyl, $C_{2-6}$ alkenyl, $C_{2-20}$ alkynyl, aryl or $C_{1-4}$ alkyl substituted by one or more groups selected from $NR^{13}R^{14}$, $COR^{13}$, $C_{3-8}$ cycloalkyl, CN, $N_3$, $OR^{13}$ and optionally substituted aryl;
- $R^7$ represents $C_{1-6}$ alkyl substituted by one or more halogen atoms, $C_{3-8}$ cycloalkyl or optionally substituted aryl;
- $R^8$, $R^9$ and $R^{10}$ each independently represent H, $C_{1-6}$ alkyl, amino, hydroxy, cyano or nitro;
- $R^{11}$ represents the side chain of a D- or L-amino acid;
- $R^{12}$ represents $NR^{13}R^{14}$, $OR^{13}$ or $R^{13}$;
- each $R^{13}$ and $R^{14}$ independently represents H, $C_{1-6}$ alkyl or optionally substituted aryl or $C_{1-4}$ alkyl; and
- $R^{15}$ represents $C_{1-6}$ alkyl;

or a pharmaceutically acceptable derivative thereof.

2. A compound as claimed in claim 1 wherein $R^1$ represents $NR^5R^6$ or $N(OR^5)R^6$.

3. A compound as claimed in claim 1 wherein Y represents $NHR^2$.

4. A compound of formula (Ia):

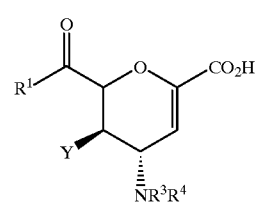

(Ia)

wherein
- $R^1$ represents $OR^5$, $SR^5$, $NR^5R^6$, $N(OR^5)R^6$ or $N(NR^5R^6)R^6$;
- Y represents H or $NHR^2$;
- $R^2$ represents a group $SO_2R^7$ or $COR^7$;
- $R^3$ represents H, $C_{1-6}$ alkyl or $C(=NR^8)NR^9R^{10}$;
- $R^4$ represents H or $C_{1-6}$ alkyl;
- $R^5$ represents H, $C_{1-20}$ alkyl, $C_{3-8}$ cycloalkyl, $C_{2-20}$ alkenyl, $C_{2-20}$ alkynyl, $CHR^{11}COR^{12}$ or $C_{1-20}$ alkyl substituted by one or more groups selected from $NR^{13}R^{14}$, $NR^{13}COR^{14}$, $CO_2R^{13}$, $OR^{13}$, $C_{3-8}$ cycloalkyl, and optionally substituted aryl;
- each $R^6$ independently represents H, $C_{1-6}$ alkyl, $C_{3-8}$ cycloalkyl, $C_{2-6}$ alkenyl, $C_{2-20}$ alkynyl, aryl or $C_{1-4}$ alkyl substituted by one or more groups selected from $NR^{13}R^{14}$, $COR^{13}$, $C_{3-8}$ cycloalkyl, CN, $N_3$, $OR^{13}$ and optionally substituted aryl;
- $R^7$ represents $C_{1-6}$ alkyl optionally substituted by one or more halogen atoms, $C_{3-8}$ cycloalkyl or optionally substituted aryl;
- $R^8$, $R^9$ and $R^{10}$ each independently represent H, $C_{1-6}$ alkyl, amino, hydroxy, cyano or nitro;
- $R^{11}$ represents the side chain of a D- or L-amino acid;
- $R^{12}$ represents $NR^{13}R^{14}$, $OR^{13}$ or $R^{13}$; and
- each $R^{13}$ and each $R^{14}$ independently represents H, $C_{1-6}$ alkyl or optionally substituted aryl or $C_{1-4}$ alkyl;

or a pharmaceutically acceptable derivative thereof.

5. A compound of formula (Ib):

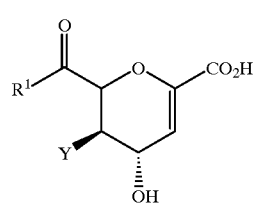

(Ib)

wherein
- $R^1$ represents $OR^5$, $SR^5$, $NR^5R^6$, $N(OR^5)R^6$ or $N(NR^5R^6)R^6$;

Y represents H or NHR$^2$;

R$^2$ represents a group SO$_2$R$^7$ or COR$^7$;

R$^3$ represents H, C$_{1-6}$ alkyl or C(=NR$^8$)NR$^9$R$^{10}$;

R$^4$ represents H or C$_{1-6}$ alkyl;

R$^5$ represents H, C$_{1-20}$ alkyl, C$_{3-8}$ cycloalkyl, C$_{2-20}$ alkenyl, C$_{2-20}$ alkynyl, CHR$^{11}$COR$^{12}$ or C$_{1-20}$ alkyl substituted by one or more groups selected from NR$^{13}$R$^{14}$, NR$^{13}$COR$^{14}$, CO$_2$R$^{13}$, OR$^{13}$, C$_{3-8}$cycloalkyl, and optionally substituted aryl;

each R$^6$ independently represents H, C$_{1-6}$ alkyl, C$_{3-8}$ cycloalkyl, C$_{2-6}$ alkenyl, C$_{2-20}$ alkynyl, aryl or C$_{1-4}$ alkyl substituted by one or more groups selected from NR$^{13}$R$^{14}$, COR$^{13}$, C$_{3-8}$ cycloalkyl, CN, N$_3$, OR$^{13}$ and optionally substituted aryl;

R$^7$ represents C$_{1-6}$ alkyl optionally substituted by one or more halogen atoms, C$_{3-8}$ cycloalkyl or optionally substituted aryl;

R$^8$, R$^9$ and R$^{10}$ each independently represent H, C$_{1-6}$ alkyl, amino, hydroxy, cyano or nitro;

R$^{11}$ represents the side chain of a D- or L-amino acid;

R$^{12}$ represents NR$^{13}$R$^{14}$, OR$^{13}$ or R$^{13}$; and each R$^{13}$ and each R$^{14}$ independently represents H, C$_{1-6}$ alkyl or optionally substituted aryl or C$_{1-4}$ alkyl;

or a pharmaceutically acceptable derivative thereof.

6. A compound of formula (Ic):

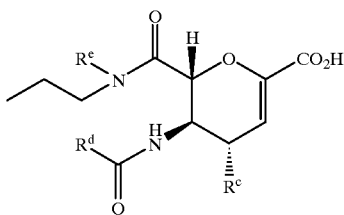

(Ic)

wherein

R$^c$ is NH$_2$ or NHC(=NH)NH$_2$;

R$^d$ is C$_{1-2}$alkyl optionally substituted by one or more fluorine atoms;

R$^e$ is C$_{2-8}$alkyl optionally substituted by phenyl, naphthyl or biphenyl, preferably ethyl substituted by phenyl, naphthyl or biphenyl;

or a pharmaceutically acceptable salt thereof.

7. A compound selected from the group consisting of:

(4S, 5R,6R)-5-acetylamino-6-dimethylcarbamoyl-4-guanidino-5,6-dihydro-4H-pyran-2-carboxylic acid;

(4S, 5R,6R)-5-acetylamino-6-(methylpropylcarbamoyl)-4-guanidino-5,6-dihydro-4H-pyran-2-carboxylic acid;

(4S, 5R,6R)-5-acetylamino-4-amino-6-dipropylcarbamoyl-5,6-dihydro-4H-pyran-2-carboxylic acid;

(4S, 5R,6R)-5-acetylamino-6-dipropylcarbamoyl-4-guanidino-5,6-dihydro-4H-pyran-2-carboxylic acid;

(4S, 5R,6R)-5-acetylamino-6-dibutylcarbamoyl-4-guanidino-5,6-dihdro-4H-pyran-2-carboxylic acid;

(4S, 5R,6R)-5-acetylamino-4-amino-6-(phenylethylpropylcarbamoyl)-5,6-dihydro-4H-pyran-2-carboxylic acid;

(4S, 5R,6R)-5-acetylamino-6-(phenylethylpropylcarbamoyl)-4-guanidino-5,6-dihdyro-4H-pyran-2-carboxylic acid;

(4S, 5R,6R)-5-acetylamino-4-amino-6-(butylpropylcarbamoyl)-5,6-dihdyro-4H-pyran-2-carboxylic acid;

(4S, 5R,6R)-5-acetylamino-4-amino-6-diethylcarbamoyl-5,6-dihydro-4H-pyran-2-carboxylic acid;

(4S, 5R,6R)-5-acetylamino-4-amino-6-(ethylpropylcarbamoyl)-5,6-dihydro-4H-pyran-2-carboxylic acid;

(4S,5R,6R)-4-Amino-6-(dipropylcarbamoyl)-5-(2,2,2-trifluoroacetylamino)-5,6-dihydro-4H-pyran-2-carboxylic acid;

(4S,5R,6R)-5-Acetylamino-4-amino-6-[(2-naphthalen-2-yl-ethyl) propylcarbamoyl]-5,6-dihydro-4H-pyran-2-carboxylic acid;

(4S,5R,6R)-5-acetylamino-4-amino-6-[(2-biphenyl-4-yl-ethyl)carbamoyl]-5,6-dihydro-4H-pyran-2-carboxylic acid;

(4S,5R,6R)-5-Acetylamino-6-[(2-cyclohexylethyl) propylcarbamoyl]-4-guanidino-5,6-dihydro-4H-pyran-2-carboxylic acid;

(4S,5R,6R)-5-Acetylamino-6-[(4-biphenylethylpropylcarbamoyl]-4-guanidino-5,6-dihydro-4H-pyran-2-carboxylic acid;

(4S,5R,6R)-4-Amino-6-(phenethylpropylcarbamoyl)-5-propionylamino-5,6-dihydro-4H-pyran-2-carboxylic acid;

and pharmaceutically acceptable derivatives thereof.

8. A pharmaceutical formulation comprising a compound as claimed in claim 1 together with a pharmaceutically acceptable carrier thereof.

9. A method for the treatment of a viral infection in a mammal comprising administration of an anti-virally effective amount of a compound as claimed in claim 1.

10. A method as claimed in claim 9 for the treatment of an influenza virus infection.

11. A process for the preparation of a compound of formula (I) as defined in claim 1 which process comprises:

(A) oxidative clearage of the glycerol sidechain of a compound of formula (II):

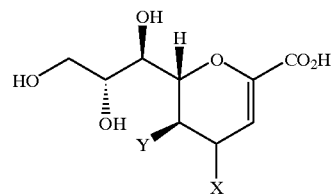

(II)

wherein X and Y are as defined for formula (I), or a protected derivative thereof; or (B) reduction of a compound (III):

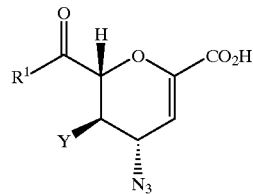

(III)

wherein R$^1$ and Y are as defined for formula (I), or a protected derivative thereof.

* * * * *